United States Patent
De Cola et al.

(10) Patent No.: US 8,734,963 B2
(45) Date of Patent: May 27, 2014

(54) COMPLEX SALTS

(75) Inventors: Luisa De Cola, Münster (DE); Matteo Mauro, Taurisano (IT); Roger Prétôt, Basel (CH)

(73) Assignee: BASF SE, Ludwigshafen (DE)

( * ) Notice: Subject to any disclaimer, the term of this patent is extended or adjusted under 35 U.S.C. 154(b) by 434 days.

(21) Appl. No.: 13/121,695

(22) PCT Filed: Sep. 22, 2009

(86) PCT No.: PCT/EP2009/062244
§ 371 (c)(1),
(2), (4) Date: Mar. 30, 2011

(87) PCT Pub. No.: WO2010/037667
PCT Pub. Date: Apr. 8, 2010

(65) Prior Publication Data
US 2011/0177630 A1   Jul. 21, 2011

(30) Foreign Application Priority Data
Oct. 2, 2008 (EP) .................................... 08105487

(51) Int. Cl.
| H01L 51/54 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ............ *C09K 11/06* (2013.01); *C07F 15/0033* (2013.01); *C07F 15/0046* (2013.01); *H01L 51/0085* (2013.01); *H01L 51/0086* (2013.01); *H01L 51/5016* (2013.01); *C09K 2211/1029* (2013.01); *C09K 2211/185* (2013.01); *Y10S 428/917* (2013.01)
USPC .......... 428/690; 428/917; 313/504; 313/506; 252/301.16; 257/40; 257/E51.044

(58) Field of Classification Search
None
See application file for complete search history.

(56) References Cited

U.S. PATENT DOCUMENTS

| 7,416,791 | B1 | 8/2008 | Carlson | |
| 2004/0110031 | A1 * | 6/2004 | Fukuda et al. | ................ 428/690 |
| 2004/0247934 | A1 | 12/2004 | Takeuchi | |
| 2005/0074630 | A1 | 4/2005 | Kanno | |
| 2005/0214576 | A1 | 9/2005 | Lamansky | |
| 2006/0022588 | A1 | 2/2006 | Tsuboyama et al. | |
| 2006/0127696 | A1 | 6/2006 | Stossel | |
| 2008/0096028 | A1 | 4/2008 | Wegh | |
| 2010/0059740 | A1 * | 3/2010 | Yersin et al. | ..................... 257/40 |
| 2011/0275818 | A1 * | 11/2011 | Yersin et al. | ..................... 546/12 |

FOREIGN PATENT DOCUMENTS

| DE | 10238903 A1 | 3/2004 | |
| EP | 1239526 A2 | 9/2002 | |
| EP | 1571193 A1 | 9/2005 | |
| WO | 2005/123095 A | 12/2005 | |
| WO | 2006/011090 A1 | 2/2006 | |
| WO | 2007/004113 A2 | 1/2007 | |
| WO | WO 2008/087031 A1 * | 7/2008 | .............. H01L 51/50 |

OTHER PUBLICATIONS

Chen et al. "Synthesis, crystal structure and photoluminescence properties of an organometallic Ir containing 2,2'-bipyridine as ancillary ligand." Chinese Journal of Inorganic Chemistry, 2008. vol. 24, No. 8, pp. 1219-1223.*
Chen et al., Abstract P.662, Poster presentation, vol. 2, p. 850 (2005).
Clemente-Leon, Inorg. Chem. vol. 45, No. 14, 2006 p. 5653-5660.
Grushin et al., Chem. Com. Royal Soc. 1494-1495 (2001).
M. Lowry et al., J. Am. Chem. Soc. 2004, 126, pp. 14129-14135.
Kam-Wing Lo, Inorg. Chem. vol. 42, No. 21, 2003 p. 6886-6897.

* cited by examiner

*Primary Examiner* — Michael H Wilson
(74) *Attorney, Agent, or Firm* — Shruti Costales

(57) ABSTRACT

Disclosed is a salt of an organometallic complex cation and an organometallic complex anion, wherein the cation as well as the anion consists of a central metal atom M of atomic weight greater than 40 associated to 2 or more ligands, at least one ligand comprising a cyclic organic moiety with a carbon atom bonding to M, and at least one ligand comprising a cyclic organic moiety with a nitrogen atom bonding to M. The novel salts may be used as conductive and/or light emitting components in electronic devices. Color emission may be chosen by selecting anion(s) and cation(s) of suitable emission characteristics.

12 Claims, No Drawings

COMPLEX SALTS

The present invention pertains to novel complex salts, a process for their preparation, electronic devices comprising the metal complexes and their use in electronic devices, especially as emitters in organic light emitting diodes (OLEDs) or light emitting electrochemical cells (LEECs), as an electrolyte or ionic liquid in a photovoltaic device or in a battery, as oxygen sensitive indicators, as phosphorescent indicators in bioassays, and as catalysts.

Organic electroluminescent compounds known for use as the active component in light-emitting devices include metal complexes containing ligands which bind to the central metal atom via a carbon and a nitrogen atom (usually C,N-binding bidentate ligands) or certain carbene ligands (e.g. C,C-binding bidentate ligands). Complexes of this class may further contain certain heteroatom-binding ligands such as those selected from derivatives of acetylacetonate, pyridylcarboxylate, 1,1-bipyridine. Some complexes of this class bearing a net charge counterbalanced by a small, non-luminescent ion have recently been proposed mainly for light emitting electrochemical cells, which require the presence of a certain level of mobile ions (WO 06/011090, WO 07/004113).

It has now been found that complex salts may be obtained which essentially consist of complex cations and complex anions, both of which have luminescent properties. Ionic mobilities by these materials in emitting layers is much lower than observable with equivalent amounts of small counterions being present, which opens further applications for the present materials.

The invention thus primarily pertains to a salt of an organometallic complex cation and an organometallic complex anion, wherein the cation as well as the anion consists of a central metal atom M of atomic weight greater than 40 associated to 2 or more ligands, at least one ligand comprising a cyclic organic moiety with a carbon atom bonding to M, and at least one ligand comprising a cyclic organic moiety with a nitrogen atom bonding to M.

The salt often comprises ions, wherein the net charge of the central metal atom M and its ligands in the cation is +1 and in the anion is −1. It may be obtained essentially free of non-complex ions, whose concentration is preferably below 5% by weight, especially below 1% by weight of the salt. Each component of the complex salt, i.e. the anions and the cations, independently, conforms to the formula I

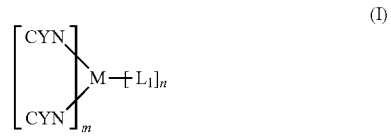
(I)

wherein M is a metal of atomic weight greater than 40,
CYC is a cyclic organic moiety with a carbon atom bonding to M,
CYN is a cyclic organic moiety with a nitrogen atom or carbene bonding to M,
$L_1$ bonding to M is selected from inorganic and organic ligands,
m is a number from 1 to 3,
n is a number from 0 to 4,
with the proviso that (m+n) is from the range 2 to 5.

In general, the (carbon) bonding site in CYC formally carries a negative charge (being derived from corresponding CYCH by abstraction of a proton); the (nitrogen or carbene) bonding site in CYN often formally carries no charge (carbene being understood in accordance with its regular meaning as a 2-bonded carbon atom containing 2 additional electrons in singlet or triplet state) or formally carries a negative charge (when the ligand is derived from corresponding CYNH by abstraction of a proton). The moieties CYC and CYN, e.g. as contained in formula I, may be separate chemical entities (i.e. monodentate ligands) or preferably may be interconnected by a chemical bond (thus together forming a bidentate ligand). Ligands of these classes are well known in the art, see for example US-2004-265633; US-2006-172150; WO04/017043; WO06/067074; and documents mentioned further above. For example, the moiety CYC may be a ring A,

representing an optionally substituted aryl group which may contain a heteroatom,
and the moiety CYN may be a ring B,

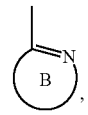

representing an optionally substituted nitrogen containing aryl group, which may contain a further heteroatom.

In preferred ligands of these classes, 2 rings are interconnected, respectively, to form a bidentate ligand of the formula:

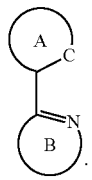

Some (formally monoanionic) ligands of this class are described in WO06/067074 (see especially page 12, line 15, to page 18, line 4, which passage is hereby incorporated by reference). Some preferred ligands of this class are described in WO 06000544, WO 07074093, WO 08101842.

A preferred group of ligands

are of the formula

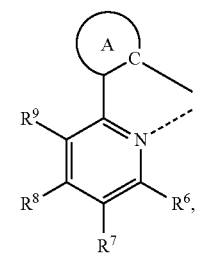

wherein $R^6$, $R^7$, $R^8$, and $R^9$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; or two substituents $R^6$, $R^7$, $R^8$, and $R^9$, which are adjacent to each other, together form a group

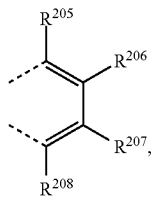

wherein $R^{205}$, $R^{206}$, $R^{207}$ and $R^{208}$ are independently of each other H, halogen or $C_1$-$C_8$alkyl or $C_1$-$C_8$alkoxy, the ring A represents an optionally substituted aryl or heteroaryl group; or a substituent on the ring A together with a residue linked to the pyridyl group, especially $R^9$, may form a ring; the alkyl group, alkenyl group, alkynyl group, aryl group, heteroaryl group, alkoxy group, alkylthio group, acyl group, and alkyloxycarbonyl group represented by $R^6$, $R^7$, $R^8$, and $R^9$ and $R^{205}$, $R^{206}$, $R^{207}$ and $R^{208}$ may be substituted.

Preferably, the salt conforms to the formula II

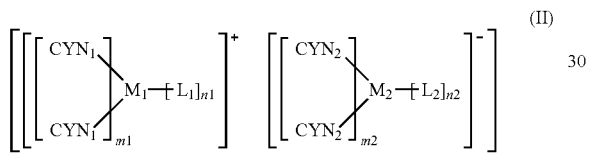

wherein $M_1$ and $M_2$ are selected from metals as defined for M, $CYC_1$ and $CYC_2$ are cyclic organic moieties as defined for CYC, $CYN_1$ and $CYN_2$ are cyclic organic moieties as defined for CYN, $L_2$ is as defined for $L_1$, $m_1$ and $m_2$ are numbers as defined for m, $n_1$ and $n_2$ are numbers as defined for n, with the proviso that i) each of $(m_1+n_1)$ and $(m_2+n_2)$ is from the range 2 to 5, ii) the sum of charges in $[CYC_1\ CYN_1]$ multiplied by m1+$L_1$ multiplied by n1+$M_1$ is +1, and iii) the sum of charges in $[CYC_2\ CYN_2]$ multiplied by m2+$L_2$ multiplied by n2+$M_2$ is −1.

In the above formulae, CYC and CYN are often interlinked by one or more chemical bonds to form a bidentate ligand, e.g. selected from

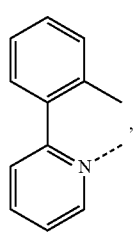
(VI-1)

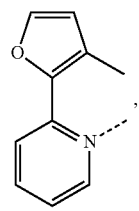
(VI-2)

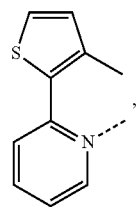
(VI-3)

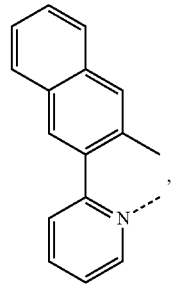
(VI-4)

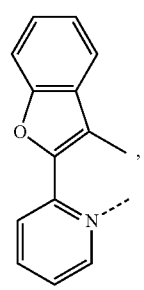
(VI-5)

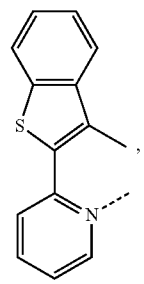
(VI-6)

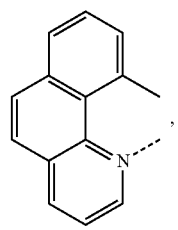
(VI-7)

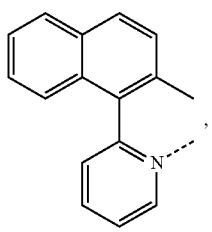 (VI-8)
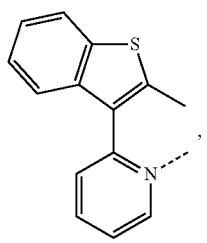 (VI-9)
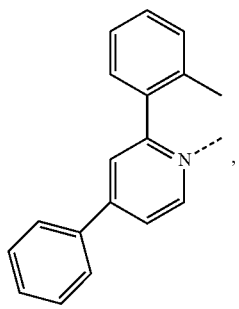 (VI-10)
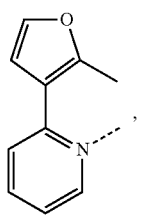 (VI-11)
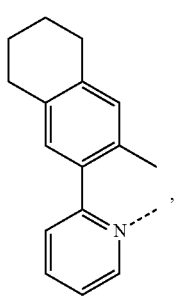 (IV-12)
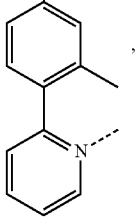 (VI-13)
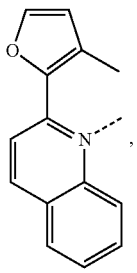 (VI-14)
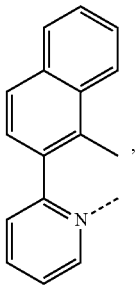 (VI-15)
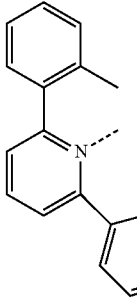 (VI-16)
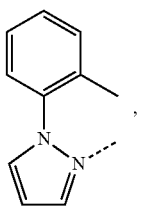 (VI-17)

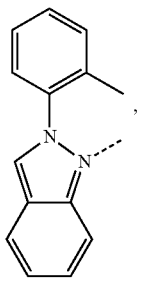
(VI-18)
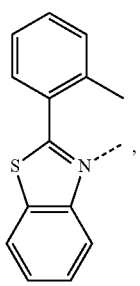
(VI-19)
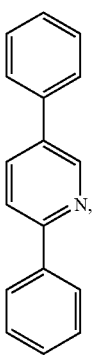
(VI-20)
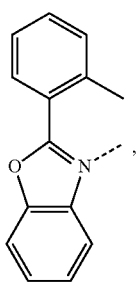
(VI-21)
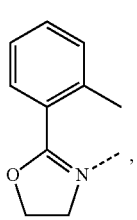
(VI-22)
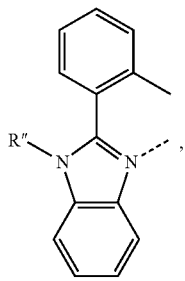
(VI-23)
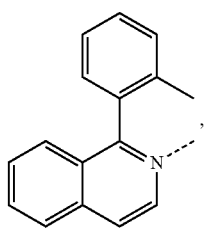
(VI-24)
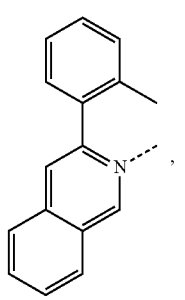
(VI-25)
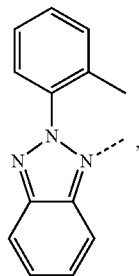
(VI-26)
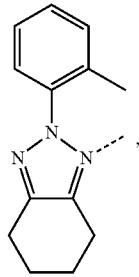
(VI-27)

-continued

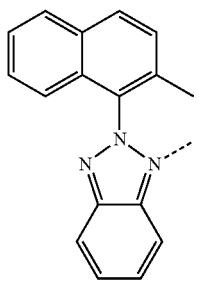
(VI-28)

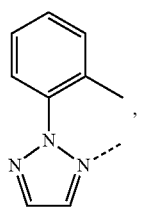
(VI-29)

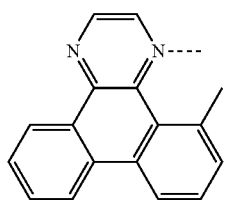
(VI-30)

wherein the dashed line in each formula indicates the N-metal bond while the straight line in each formula indicates the carbon-metal bond, and wherein carbon atoms not bonding to metal are unsubstituted or substituted; with the following features being preferred:

$L_1$ as a cationic ligand is selected from mono- and bidentate organic cationic ligands;

$L_1$ as a neutral ligand is selected from mono- and bidentate organic ligands;

$L_1$ as an anionic ligand is selected from mono- and bidentate organic anionic ligands and monodentate inorganic ligands;

M is selected from Tl, Pb, Bi, In, Sn, Sb, Te, Mo, Cr, Mn, Ta, V, Zn, Fe, Ni, Co, Rh, Re, Os, Ag, Au, lanthanides such as Eu, Tb, Nd, Yb, Er, and especially Cu, Ru, Ir, Pt, Pd; and any substituent, if present, is selected from halogen, hydroxy, $C_1$-$C_8$alkyl, $C_1$-$C_8$fluoroalkyl, $C_1$-$C_8$alkoxy, phenyl, phenyloxy, COR, OCOR, COOR, $SO_2R$, CN, NHR, NRR', and ionic substituents —X'-(spacer)$_x$-Y'; where R, R' independently are selected from $C_1$-$C_{12}$alkyl or together are pentylene or $(CH_2)_2O(CH_2)_2$ or $(CH_2)_2NH(CH_2)_2$ and R may also be hydrogen; X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from $COO^-$, $OCOO^-$, $SO_3^-$, $OSO_3^-$, $PO_3^{2-}$, $OPO_3^{2-}$, or a cationic group selected from $NR_3^+$.

Further ligands CYN (and/or, if desired, L) of interest are those of the carbene type, e.g. as disclosed in US2006/258043 or WO06/067074. Examples are ligands containing an acyclic nucleophilic carbene, preferably a group of the following formula

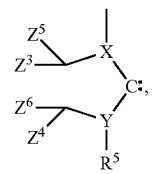

wherein X=Y=N, B, or P;

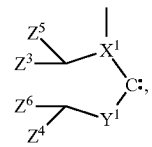

wherein $X^1$ is N, or P and $Y^1$ is S, or O; >$SiX^2X^3$, or >$CZ^5Z^3$, wherein $X^2$ and $X^3$ are independently of each other $C_1$-$C_4$alkyl and $R^5$, $Z^3$, $Z^4$, $Z^5$ and $Z^6$ are as defined below.

Examples that specify the possibilities for the group designated above are as follows:

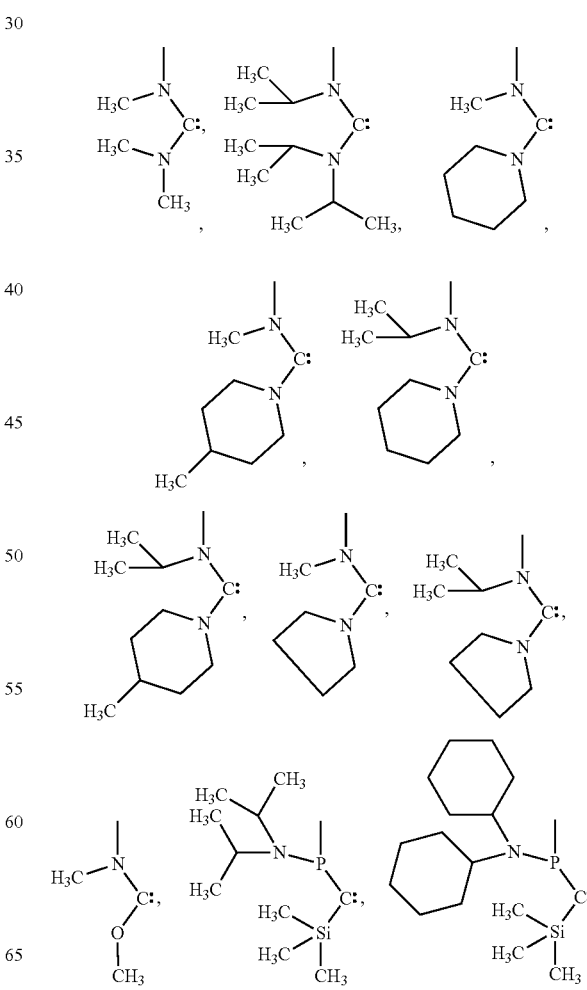

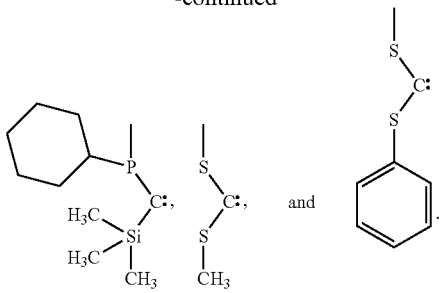

Cyclic carbenes,

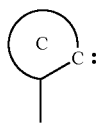

are preferred against acyclic carbenes, examples of CYN in this meaning are as follows:

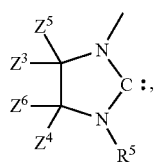

especially

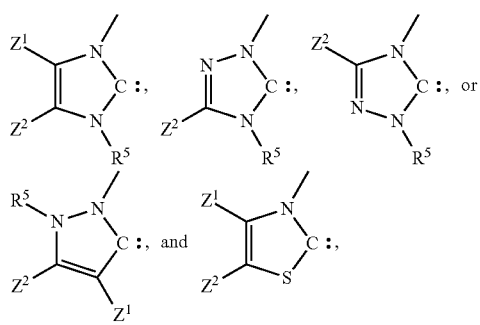

wherein

R⁵ is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy; and $Z^1$, $Z^2$, $Z^3$, $Z^4$, $Z^5$ and $Z^6$ are independently of each other selected from the group consisting of hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

In said embodiment the ligand

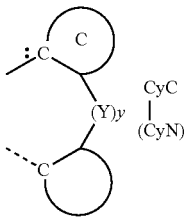

is preferably a group of formula

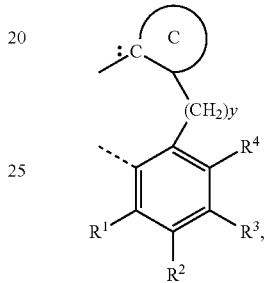

wherein $R^1$ to $R^4$ are substitutents and can be taken together to form a ring, y is 0, or 1, especially 0, the group C,

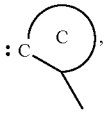

is a group (nucleophilic carbene) of the following formula

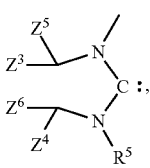

especially

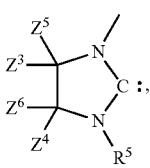

very especially

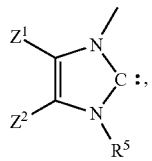

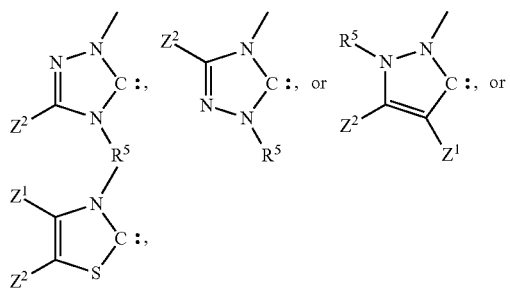

wherein
R⁵ is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy; and $Z^1$, $Z^2$, $Z^3$, $Z^4$, $Z^5$ and $Z^6$ are independently of each other selected from the group consisting of hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

Further specific examples of nucleophilic carbene ligands, especially bidentate ones of the

CyC
|
CyN type, are as disclosed in WO06/067074.

Further examples are the ligands

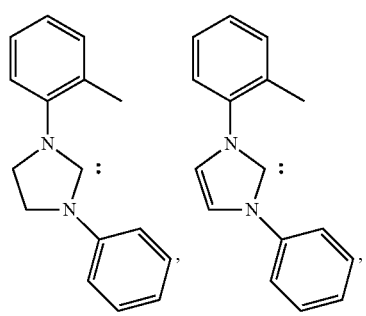

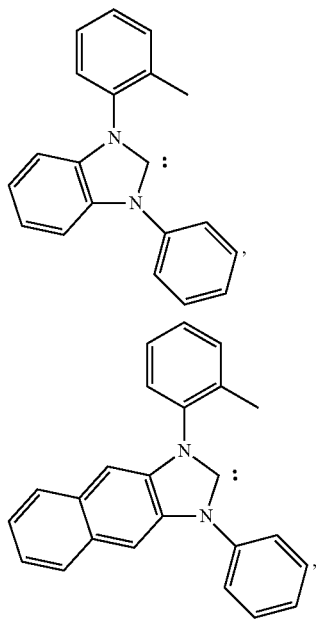

wherein open bonds indicate the carbon-metal, and 2 points indicate the carbene-metal binding site, and wherein each ligand is unsubstituted or substituted.

Preferred examples for ligands

CyC
|
CyN include those of formulae

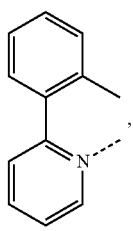

(VI-1)

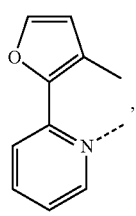

(VI-2)

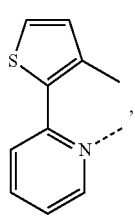

(VI-3)

-continued
(VI-4)
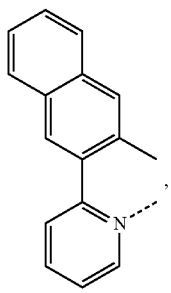
(VI-5)
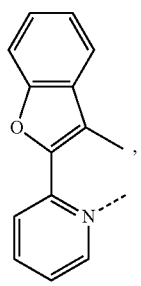
(VI-6)
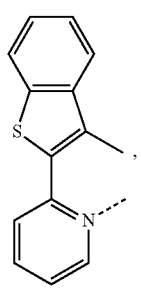
(VI-7)
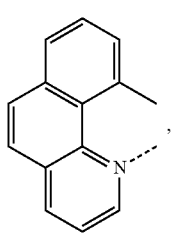
(VI-8)
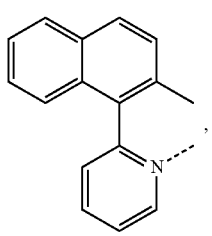
(VI-9)
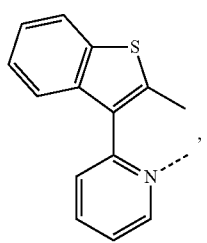
-continued
(VI-10)
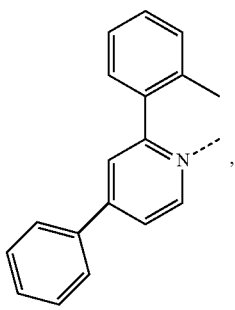
(VI-11)
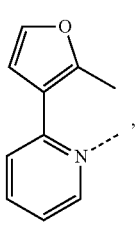
(IV-12)
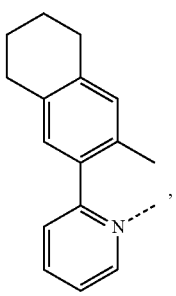
(VI-13)
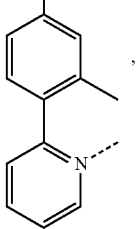
(VI-14)
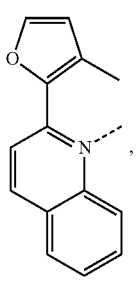

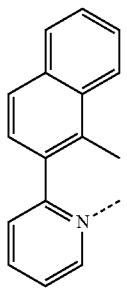 (VI-15)
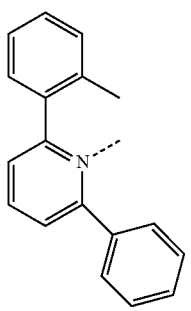 (VI-16)
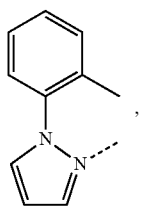 (VI-17)
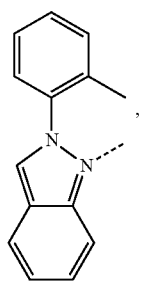 (VI-18)
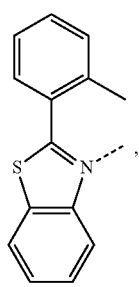 (VI-19)
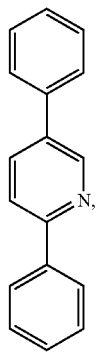 (VI-20)
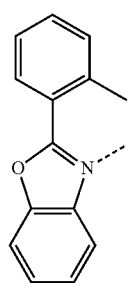 (VI-21)
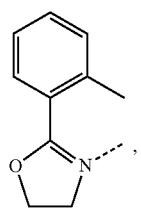 (VI-22)
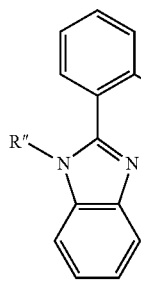 (VI-23)
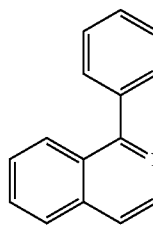 (VI-24)

(VI-25)

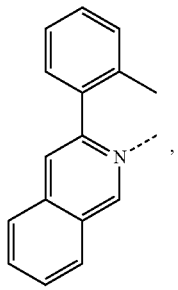
(IV-26)

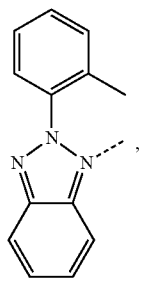
(IV-27)

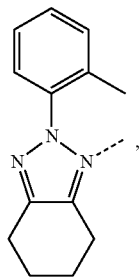
(IV-28)

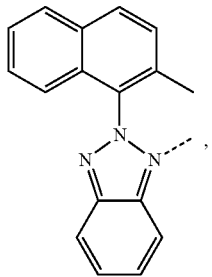
(IV-29)

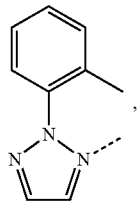
(IV-30)

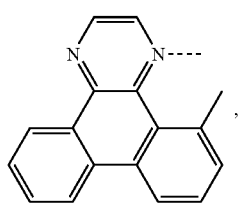

wherein the dashed line in each formula indicates the N-metal bond while the straight line in each formula indicates the carbon-metal bond, and wherein carbon atoms not bonding to metal are unsubstituted or substituted as explained further below, and R" is as defined for R further below.

$L_1$ and, if present, $L_2$ are often selected from monodentate halogenides, cyano, phosphines, and organic bidentate ligands having N, O, P, B, or S, or C in the case of carbene ligands, as coordinating atoms and forming 5- or 6-membered rings when coordinated to the metal, the organic bidentate ligands being preferably selected from

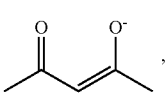
(X-1)

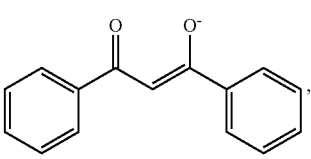
(X-2)

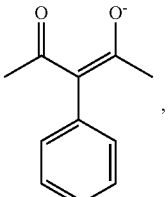
(X-3)

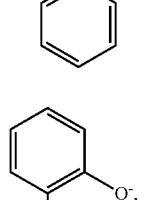
(X-4)

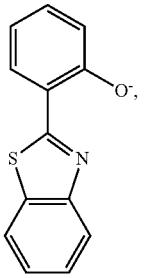
(X-5)

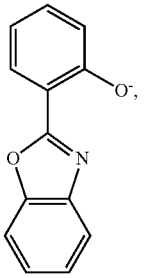
(X-6)

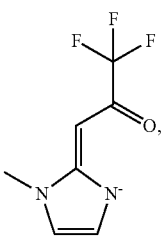

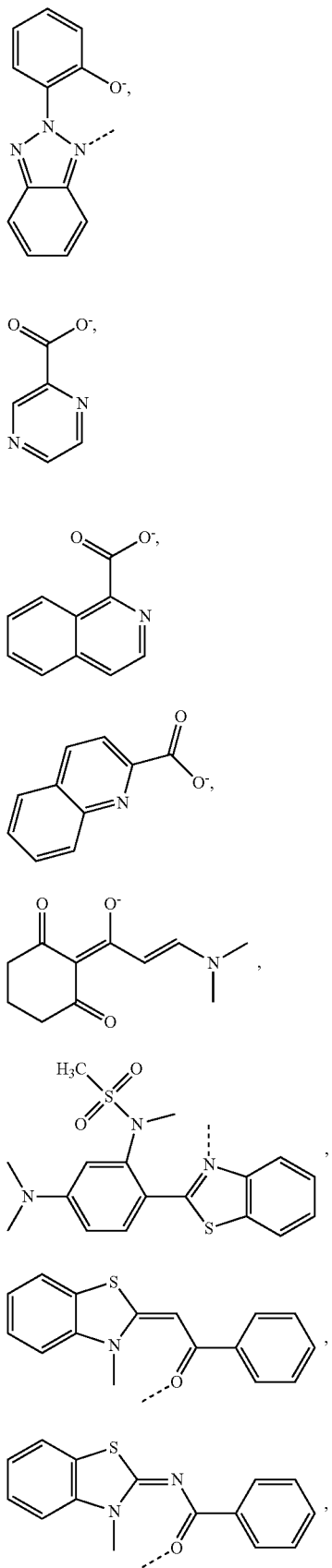
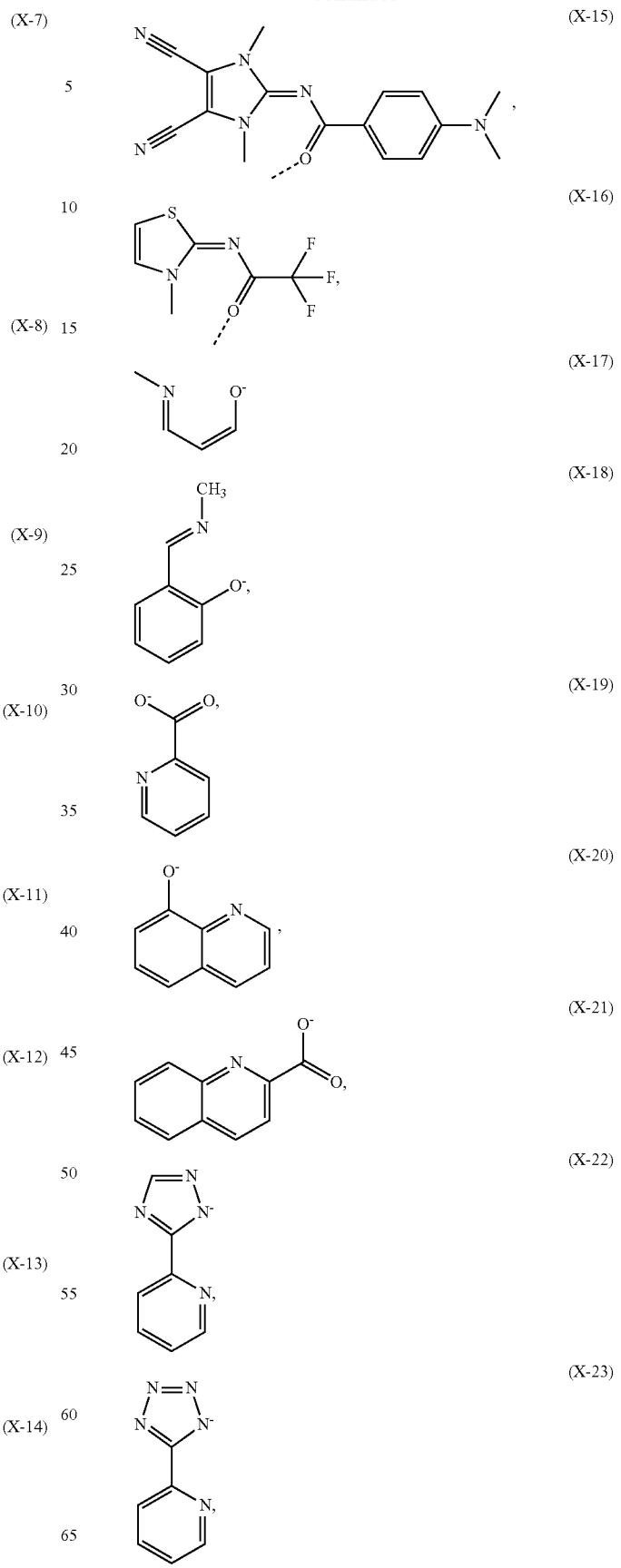

(X-24) 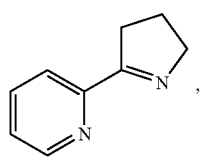
(X-25) 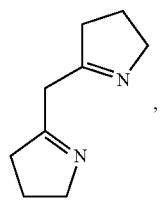
(X-26) 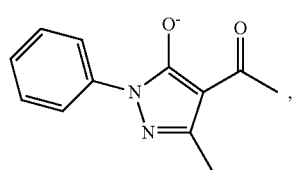
(X-27) 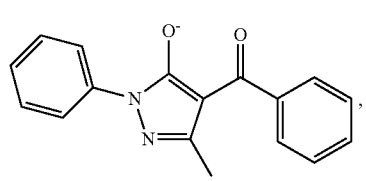
(X-28) 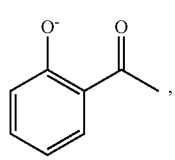
(X-29) 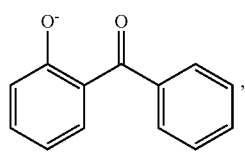
(X-30) 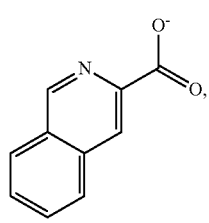
(X-31) 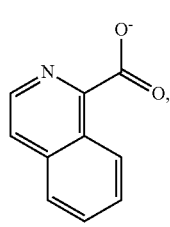
(X-32) 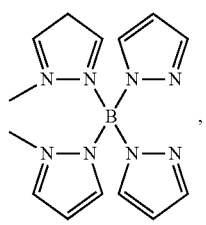
(X-33; WO03040256] 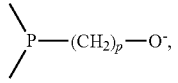
(X-34) 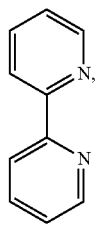
(X-35) 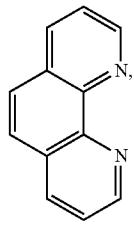
(X-36) 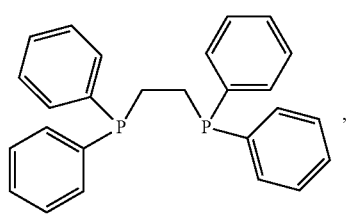
(X-37) 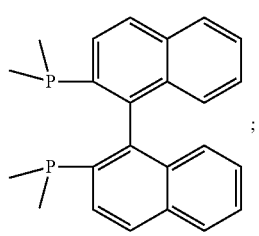
(X-38) 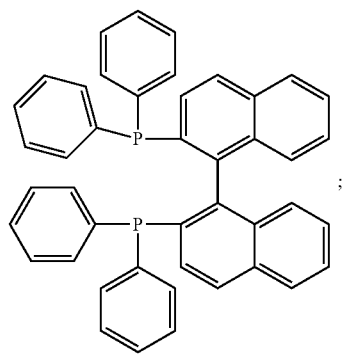

-continued

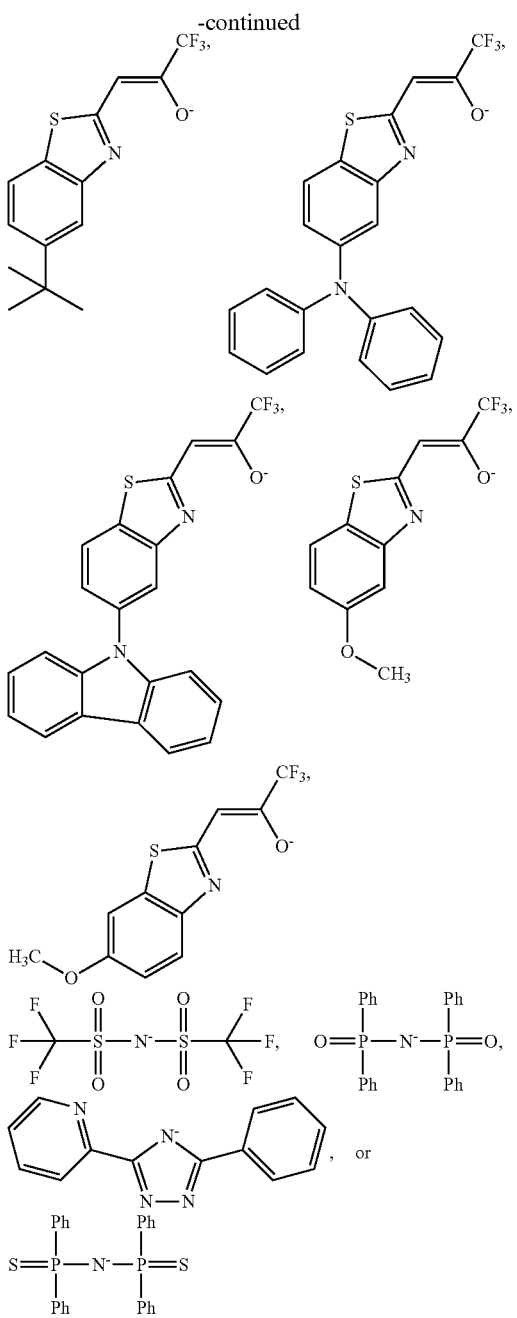

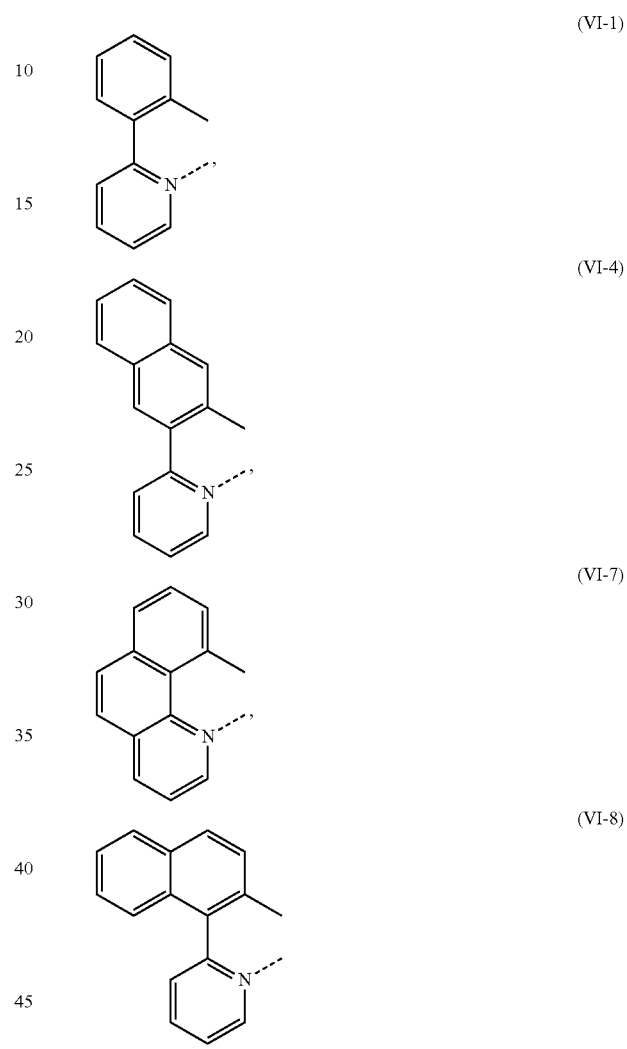

wherein Ph stands for phenyl, each of which is unsubstituted or substituted on one or more of its carbon atoms by a substituent as described below and/or by $C_6$-$C_{18}$aryl, especially phenyl;

the substituent, if present, being selected from halogen, hydroxy, $C_1$-$C_8$alkyl, $C_1$-$C_8$fluoroalkyl, $C_1$-$C_8$alkoxy, phenyl, phenyloxy, COR, OCOR, COOR, $SO_2R$, CN, NHR, NRR', and ionic substituents —X'-(spacer)$_x$-Y'; where R, R' independently are selected from $C_1$-$C_{12}$alkyl or together are pentylene or $(CH_2)_2O(CH_2)_2$ or $(CH_2)_2NH(CH_2)_2$ and R may also be hydrogen; X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from $COO^-$, $OCOO^-$, $SO_3^-$, $OSO_3^-$, $PO_3^{2-}$, $OPO_3^{2-}$, or a cationic group selected from $NR_3^+$.

In certain salts of specific interest, independently, the metal M is selected from Ir and Pt, CYC and CYN are interconnected to commonly form a bidentate ligand selected from 2-phenylpyridines of the formulae which are unsubstituted or substituted by halogen, $C_1$-$C_4$haloalkyl, $C_1$-$C_4$alkyl or $C_1$-$C_4$alkoxy and/or by a ionic substituent;

$L_1$ as a neutral ligand is selected from bipyridine and phenanthroline, each of which is unsubstituted or substituted by halogen, $C_1$-$C_4$haloalkyl, $C_1$-$C_4$alkyl, $C_1$-$C_4$alkoxy, phenyl, halophenyl;

$L_1$ as a cationic ligand is selected from the above neutral ligands which carry, in addition, a cationic substituent;

$L_1$ as an anionic ligand is selected from halogenide and cyano; pyridylcarboxylate which is unsubstituted or substituted by halogen, $C_1$-$C_4$haloalkyl, $C_1$-$C_4$alkyl, $C_1$-$C_4$alkoxy and/or an anionic substituent; and from the above neutral ligands which carry, in addition, an anionic substituent;

any ionic substituent is selected from groups of the formula —X'-(spacer)$_x$-Y'; where X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from COO$^-$, SO$_3^-$, OSO$_3^-$, or a cationic group selected from NR$_3^+$, and R is H or $C_1$-$C_{12}$alkyl.

Electroluminescent devices based on the present compounds show good device stability/lifetime, high turn-on speed for light emission, good efficiency even when operated at high brightness. The present compounds may be designed to provide the full range of luminescent colours. This allows for the design of new materials containing combinations of the present compounds for white light applications (including lighting, backplanes, signage, displays etc.).

The charge of the anions and cations, which are the essential elements in the present complex salt, usually adds up as a net value of formal charges of their constituents; charges may be located at the metal centre or may be a part (substituent) of the CYN, CYC, $L_1$ and/or $L_2$ ligands.

The metal M is generally a metal with an atomic weight of greater than 40. Preferably the metal M is selected from Tl, Pb, Bi, In, Sn, Sb, Te, especially Mo, Cr, Mn, Ta, V, Zn, Cu, Fe, Ru, Ni, Co, Ir, Pt, Pd, Rh, Re, Os, Ag and Au, and/or lanthanides such as Eu, Tb, Nd, Yb, Er. More preferably, the metal is selected from Ir and Ru as well as Cu, Ag, Au, Pt and Pd, wherein Ir and Pt are most preferred.

The number of ligands, monodentate and/or ("chelating") bidentate, generally is determined by the number of binding sites of the metal. The metal may be neutral or, more common, in a suitable oxidation state commonly known in the art. For example, Ir is most preferably in the formal oxidation state 3+ (usually 6-fold coordination), Ru in the formal oxidation state 2+ (usually 6-fold coordination), Pt and Pd and Au and Zn in the formal oxidation state 2+ (usually tetracoordinated), Ag and Cu in the formal oxidation state 1+ (usually tetracoordinated).

Thus, if all ligands are bidentate, the following coordinations usually apply:

If M is Co or Fe, especially Ir or Ru or Rh, (n+m) is preferably 3, especially where n is 1 and m is 2; if M is Ni, Rh, or especially Pd, Ru, or Pt, (n+m) is preferably 2.

In preferred complexes of the invention, the central atom M is obtained from a salt of a metal cation of charge 2+ (e.g. Pt2+) or especially 3+ (e.g. Ir3+).

In certain complexes of special interest, all ligands are bidentate and n is 1 and m is 2.

$L_1$ (and $L_2$) often are selected from monodentate inorganic or organic ligands and bidentate organic ligands commonly known in the art, such as halogenides (especially F$^-$, Cl$^-$), cyano (CN$^-$), phosphines (such as PCy$_3$). Some preferred monoanionic bidentate ligands of this class are described in WO06/067074 (see especially page 18, line 5, to page 22, line 5, which passage is hereby incorporated by reference).

Monodentate ligands are preferably monoanionic. Such ligands can have O or S as coordinating atoms, with coordinating groups such as alkoxide, carboxylate, thiocarboxylate, dithiocarboxylate, sulfonate, thiolate, carbamate, dithiocarbamate, thiocarbazone anions, sulfonamide anions, and the like. In some cases, ligands such as β-enolates can act as monodentate ligands. The monodentate ligand can also be a coordinating anion such as halide, nitrate, sulfate, hexahaloantimonate, and the like. Examples of suitable monodentate ligands are shown below:

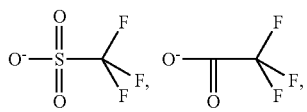

-continued

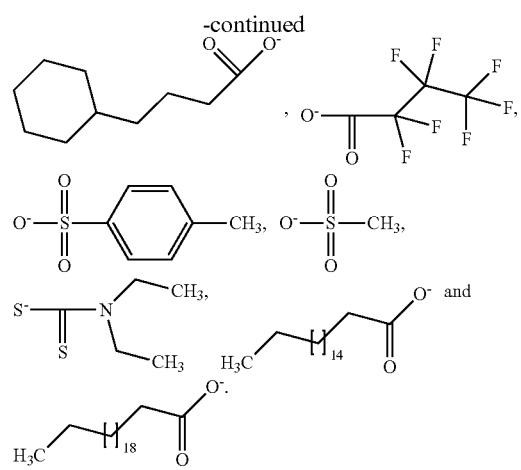

Useful monodentate ligands largely are commercially available.

In a preferred embodiment of the present invention the ligand $L_1$ (and $L_2$) is a bidentate ligand. In general these ligands have N, O, P, or S as coordinating atoms and form 5- or 6-membered rings when coordinated to the metal. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; diarylphosphinoalkanols (diarylphosphinoalkoxide ligands); bipyridines.

Bidentate ligands of specific interest are often selected from (2H-benzo)triazole, o-phenylpyridine, each of which may be unsubstituted or substituted.

Ligand $L_1$ (and $L_2$) often conforms to the formula III

 (III)

wherein G' stands for an organic bridging group or a direct bond, $D_3$ stands for an organic moiety containing an electron donating heteroatom selected from nitrogen, oxygen, sulphur, phosphorus, and $D_4$ stands for an organic moiety containing an anionic heteroatom selected from nitrogen, sulphur;

which may, for certain ligands A, be formulated as formula IV

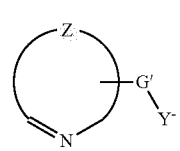 (IV)

wherein

Z is an organic bridging group forming, together with the nitrogen atom, an unsaturated or aromatic 4- to 8-membered ring, which optionally may be substituted, and Y$^-$ is an aliphatic or aromatic, cyclic or non-cyclic organic moiety binding to the central Cu atom by anionic nitrogen.

In preferred ligands of the formula III, G' stands for a direct bond;

$D_3$ stands for an unsaturated or aromatic heterocyclic moiety of 5 to 14 ring atoms, such as a tertiary aromatic amino moiety or a corresponding oxa or thia moiety;

$D_4$ stands for an anion of an unsaturated or aromatic N-heterocyclic moiety of 5 to 14 ring atoms;

or the ligand $D_3$-G'-$D_4$ stands for a system of at least 2 annealed rings of 8 to 14 ring atoms according to the formula V

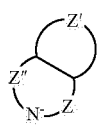
(V)

which optionally may be substituted, and wherein Z' is an organic bridging group containing at least one electron donating heteroatom selected from nitrogen, oxygen, sulphur, phosphorus, and forming, together with the carbon atoms it bonds to, an unsaturated or aromatic 4- to 8-membered ring, which optionally may be substituted; and wherein Z and Z" independently are selected from organic bridging groups and a direct bond completing together, with the nitrogen atom, an unsaturated or aromatic 4- to 8-membered ring, which optionally may be substituted and wherein at least one of Z and Z" is not a direct bond.

$D_3$ is often selected from pyridyl, pyrimidyl, pyridazyl, pyrazyl, pyranyl, cumaryl, pteridyl, thiophenyl, benzothiophenyl, furyl, benzofuryl, thiazolyl, thienothienyl, dithiaindacenyl, chinolyl, isochinolyl, chinoxalyl, acridyl, azanaphthyl, phenanthrolyl, triazinyl, thienyl,

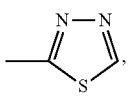

each of which is unsubstituted or substituted;

$D_4$ from anionic moieties as obtainable after N-deprotonation of a residue purinyl, pyrryl, indyl, carbazolyl, triazolyl, benzotriazolyl, pyrazolyl, benzopyrazolyl, imidazolyl, benzimidazolyl, tetrazolyl, each of which is unsubstituted or substituted;

or the ligand $D_3$-G'-$D_4$ is of the formula V, wherein Z' is an organic bridging group bonding to the 2 connecting carbon atoms and selected from NCHCHCH, CHNCHCH, NNCHCH, NCHNCH, NCHCHN, NNNCH, NNCHN, OCHCH, CHOCH, OCHN, SCHCH, SCHN, CHSCH, whose carbon atoms optionally may be substituted; and Z"—N⁻—Z is an organic bridging group bonding to the 2 connecting carbon atoms and selected from N⁻CHCH, CHN⁻CH, N⁻CHN, N⁻NCH, N⁻NN, whose carbon atoms, if present, optionally may be substituted;

especially where a heteroatom from $D_3$ or Z', and the anionic nitrogen, are in 1,3- or 1,4- or 1,5-position.

Some further useful ligands are derived from 3-pyridyl-substituted 1,2,4-triazole of the below formulae

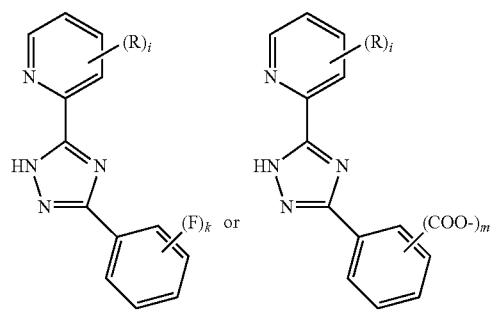

wherein i and m independently are 0, 1 or 2;

k is from the range 3-5;

R independently is $C_1$-$C_{12}$alkyl, $C_2$-$C_8$alkenyl, halogen, nitro, amino, methoxy.

Other preferred bidentate organic ligands $L_1$ (and/or $L_2$) often are selected from

(X-1)

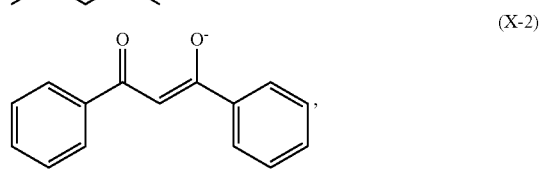
(X-2)

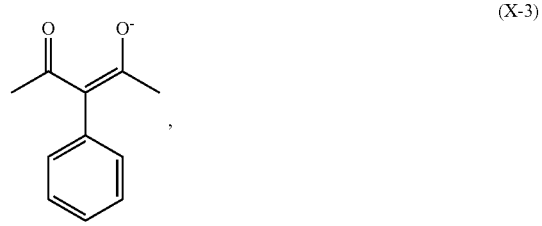
(X-3)

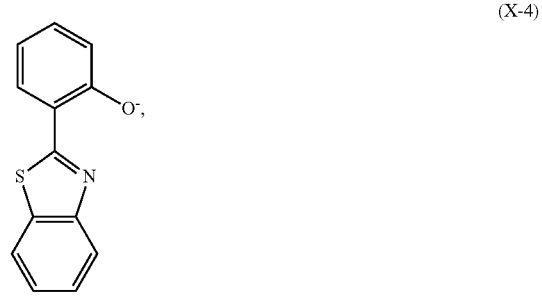
(X-4)

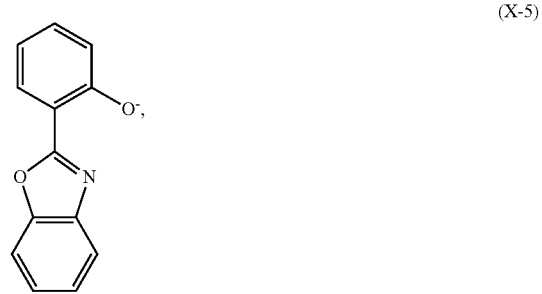
(X-5)

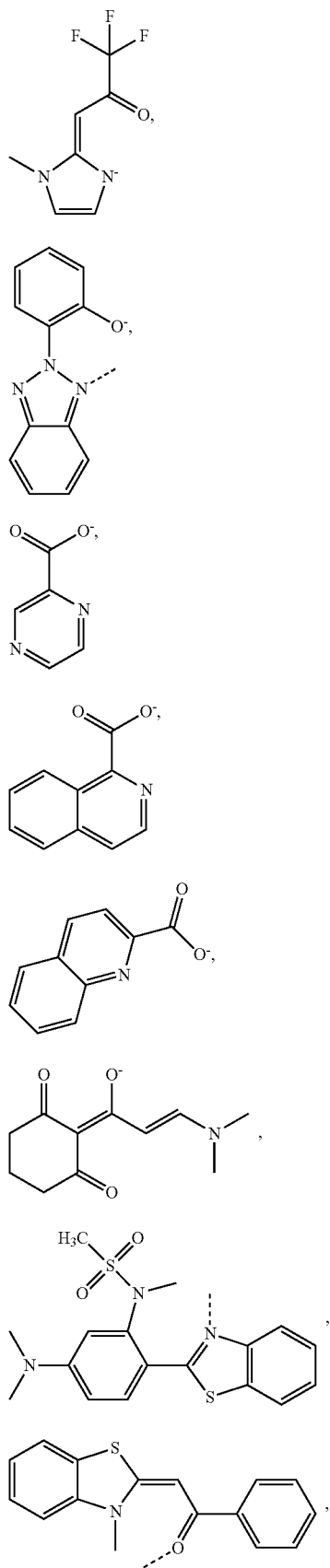
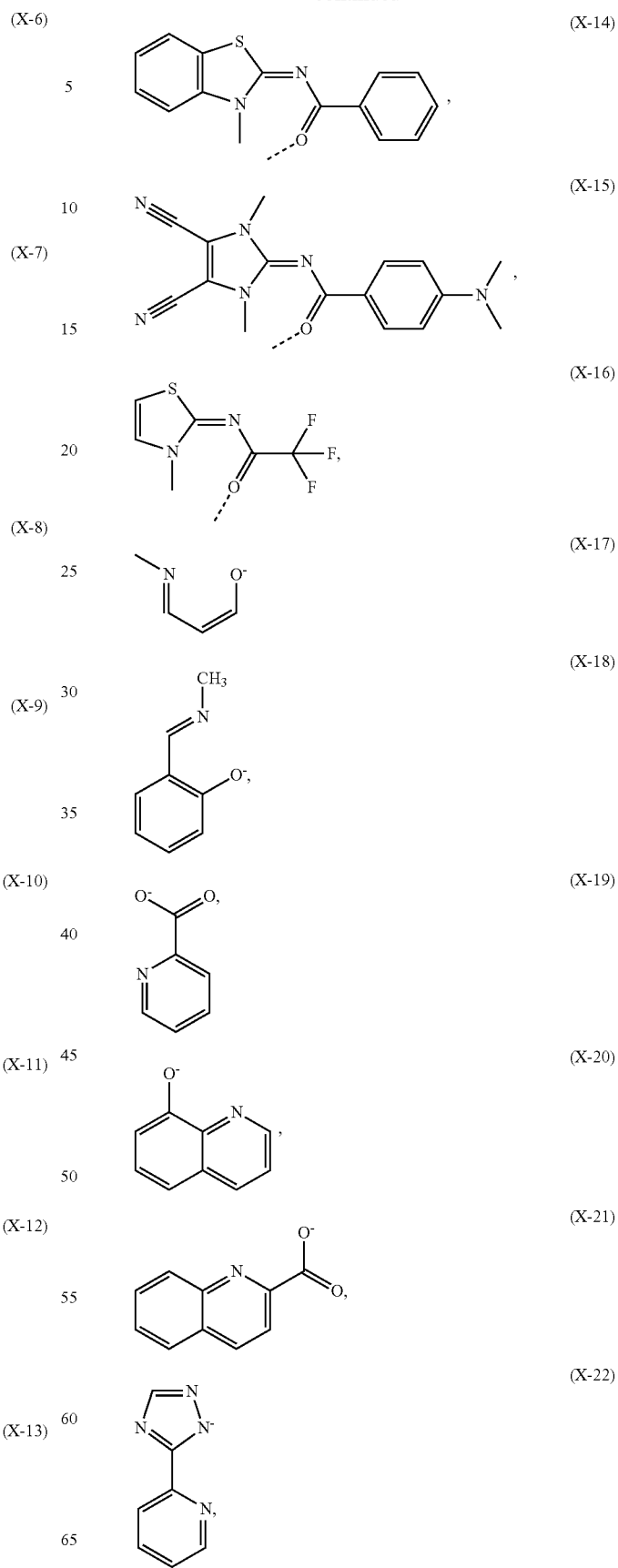

(X-23) 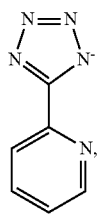
(X-24) 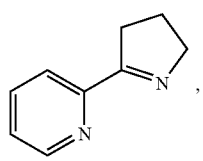
(X-25) 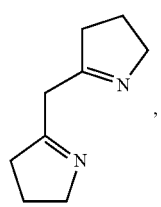
(X-26) 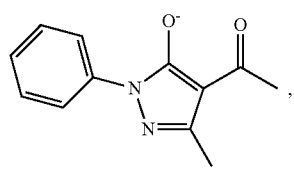
(X-27) 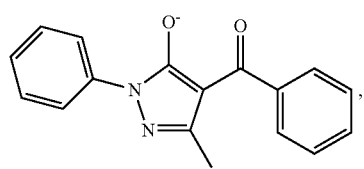
(X-28) 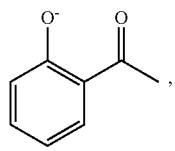
(X-29) 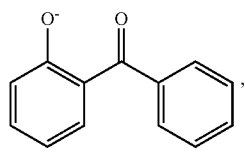
(X-30) 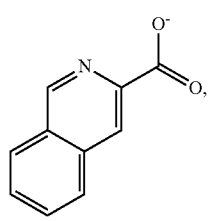
(X-31) 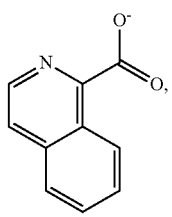
(X-32) 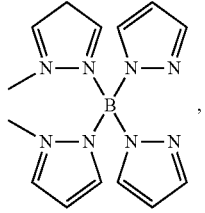
(X-33; WO03040256] 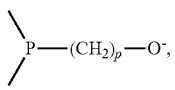
(X-34) 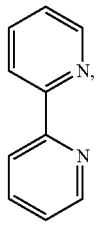
(X-35) 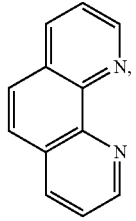
(X-36) 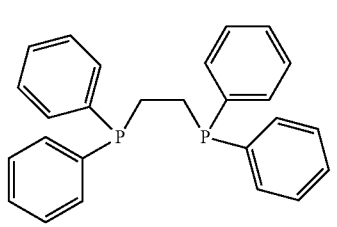
(X-37) 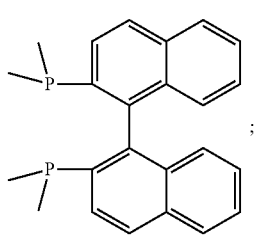

-continued

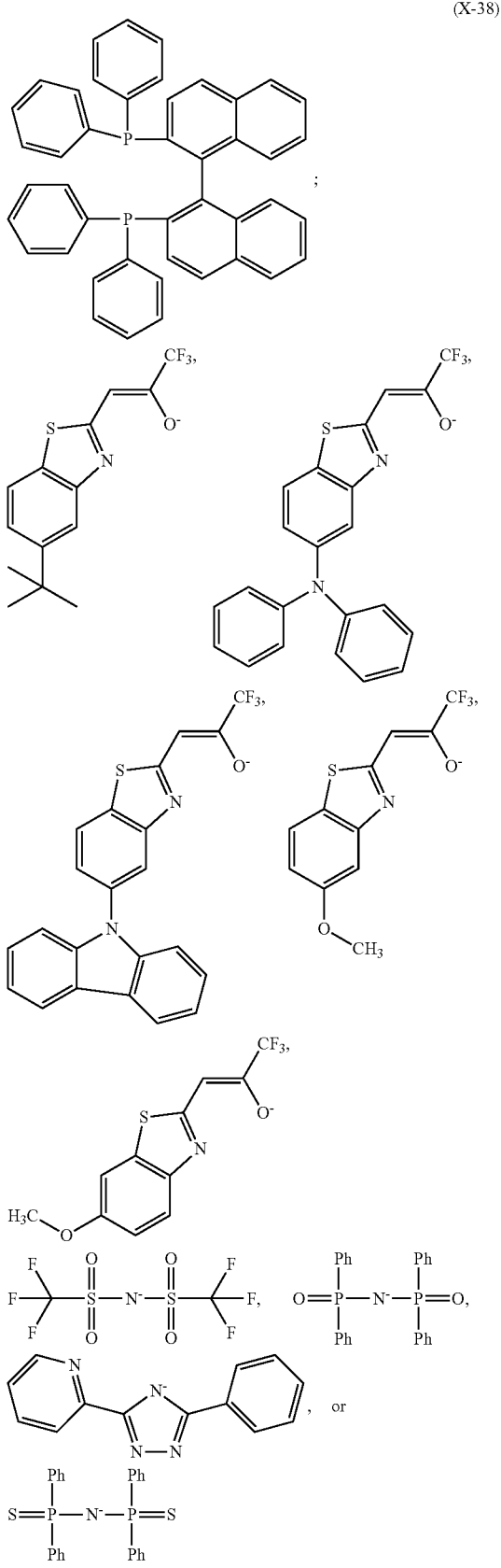

wherein Ph stands for phenyl, each of which is unsubstituted or substituted on one or more of its carbon atoms by a substituent as described below and/or by $C_6$-$C_{18}$aryl, especially phenyl.

Examples of suitable phosphino alkoxide ligands (X-33, WO03040256) are listed below:
3-(diphenylphosphino)-1-oxypropane [dppO]
1,1-bis(trifluoromethyl)-2-(diphenylphosphino)-ethoxide [tfmdpeO].

$L_1$ (and $L_2$) as a monoanionic bidentate ligand may also be one of the formula III
(see WO08098851)

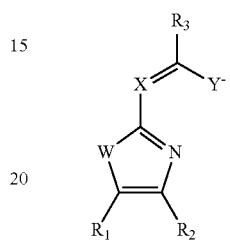

(III)

wherein
W is selected from O, S, $NR_4$, $CR_5R_6$,
X is N or $CR_7$,
Y is selected from O, S, $NR_8$;
$R_1$, $R_2$, $R_4$, $R_5$, $R_6$ independently are H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl;
or $R_1$, $R_2$ independently may stand for a substituent selected from halogen, $C_1$-$C_{18}$alkoxy, $C_1$-$C_{18}$alkylthio, $C_1$-$C_{18}$acyl, $C_5$-$C_{10}$aryl, $C_3$-$C_{12}$cycloalkyl, $C_1$-$C_{18}$acyloxy, $C_5$-$C_{10}$aryloxy, $C_3$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R'', PORR', PO(OR)R', PO(OR)$_2$, PO(NHR)$_2$, PO(NRR')$_2$, CN, $NO_2$, NHR, NRR', NH—NHR, NH—NRR', CONROH;
R, R' and R'' independently are selected from $C_1$-$C_{12}$alkyl, $C_5$-$C_{10}$aryl, $C_3$-$C_{12}$cycloalkyl, preferably from $C_1$-$C_6$alkyl, phenyl, cyclopentyl, cyclohexyl;
and R may also be hydrogen;
or the neighbouring residues $R_1$ and $R_2$ form an organic bridging group completing, together with the carbon atoms they are bonding to, a carbocyclic or heterocyclic, non-aromatic or preferably aromatic ring of 5 to 7 ring atoms in total, which optionally may be substituted;
$R_7$, if present, together with its neighbouring residue $R_3$ forms an organic bridging group completing, with the carbon atoms they are bonding to, a carbocyclic or heterocyclic, non-aromatic or preferably aromatic ring of 5 to 7 ring atoms in total, which optionally may be substituted; and in case that W is O, $NR_4$, $CR_5R_6$ and/or Y contains a nitrogen atom, $R_7$ also embraces the meanings given for $R_4$;
or $R_3$ is H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl;
$R'_3$ is unsubstituted or substituted $C_1$-$C_{18}$alkylene, unsubstituted or substituted $C_2$-$C_{18}$alkenylene, unsubstituted or substituted $C_5$-$C_{10}$arylene, unsubstituted or substituted $C_2$-$C_{10}$heteroarylene, $C_2$-$C_{18}$diacylene;
$R_8$ is hydrogen or a substituent.

In the compounds and ligands described above, any substituent, if present, preferably is selected from halogen, hydroxy, $C_1$-$C_8$alkyl, $C_1$-$C_8$fluoroalkyl, $C_1$-$C_8$alkoxy, phenyl, phenyloxy, COR, OCOR, COOR, $SO_2R$, CN, NHR, NRR', and ionic substituents —X'-(spacer)$_x$-Y'; where R, R' independently are selected from $C_1$-$C_{12}$alkyl or together are pentylene or $(CH_2)_2O(CH_2)_2$ or $(CH_2)_2NH(CH_2)_2$ and R may also be hydrogen; X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from $COO^-$, $OCOO^-$, $SO_3^-$, $OSO_3^-$, $PO_3^{2-}$, $OPO_3^{2-}$, or a cationic group selected from $NR_3^+$.

In case of the hexacoordinated metal complexes containing 2 different types of bidentate ligands, which complexes form an embodiment of specific interest within the present invention (e.g. with M being Ir, or Ru, see above), three isomers can exist:

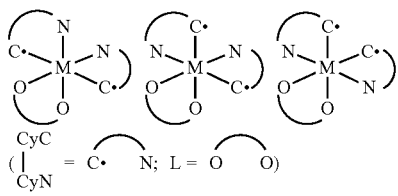

In some cases mixtures of isomers are obtained. Often the mixture can be used without isolating the individual isomers. The isomers can be separated by conventional methods, as described in A. B. Tamayo et al., J. Am. Chem. Soc. 125 (2003) 7377-7387.

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one triangular face of the octahedron. The term "meridional" is intended to mean one isomer of a complex, $Ma_3b_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to," when referring to 2 substituents on one or more aromatic rings, mean substituents which may form an annellated aromatic ring. The term "annellated aromatic ring" denotes a ring formed by sp2-hybridized atoms which bonds to at least 2 atoms of another aromatic ring. The phrase "adjacent to," when used to refer to layers in a device, does not necessarily mean that one layer is immediately next to another layer. The term "photoactive" refers to any material that exhibits electroluminescence and/or photosensitivity.

Any carbocyclic or heterocyclic, non-aromatic or preferably aromatic ring of 5 to 7 ring atoms in total formed by two neighbouring residues as an organic bridging group together with their anchor atoms often is selected from aryl, heteroaryl, cycloalkyl, or cycloaliphatic unsaturated moieties as explained below.

Where aryl (e.g. in $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl. The term aryl mainly embraces $C_1$-$C_{18}$aromatic moieties, which may be heterocyclic rings (also denoted as heteroaryl) containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl, especially phenyl. Heteroaryl such as $C_4$-$C_{18}$heteroaryl stands for an aryl group containing at least one heteroatom, especially selected from N, O, S, among the atoms forming the aromatic ring; examples include pyridyl, pyrimidyl, pyridazyl, pyrazyl, thienyl, benzothienyl, pyrryl, furyl, benzofuryl, indyl, carbazolyl, benzotriazolyl, thiazolyl, chinolyl, isochinolyl, triazinyl, tetrahydronaphthyl, thienyl, pyrazolyl, imidazolyl. Preferred are $C_4$-$C_{18}$aryl, e.g. selected from phenyl, naphthyl, pyridyl, tetrahydronaphthyl, furyl, thienyl, pyrryl, chinolyl, isochinolyl, anthrachinyl, anthracenyl, phenanthryl, pyrenyl, benzothiazolyl, benzoisothiazolyl, benzothienyl, especially $C_6$-$C_{10}$aryl; most preferred is phenyl, naphthyl.

Halogen denotes I, Br, Cl, F, preferably Cl, F, especially F. Haloalkyl denotes alkyl substituted by halogen; this includes perhalogenated alkyl such as perfluoroalkyl, especially $C_1$-$C_4$perfluoroalkyl, which is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH=CH—]$_n$ or —[CH=C(CH$_3$)—]$_n$, where n may be, for example, from the range 2-50. Where not defined otherwise, preferred alkyl contains 1-22 carbon atoms; preferred alkenyl and alkinyl each contains 2-22 carbon atoms, especially 3-22 carbon atoms.

Where indicated as interrupted, any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR10-, —S— occur in one radical, they often are identical.

The term alkyl, wherever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

Haloalkyl denotes alkyl substituted by halogen; this includes perhalogenated alkyl such as perfluoroalkyl, especially $C_1$-$C_4$perfluoroalkyl, which is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

Aralkyl is, within the definitions given, usually selected from $C_7$-$C_{24}$aralkyl radicals, preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl or 3-methyl-5-(1',1',3',3')-tetramethylbutyl)-benzyl.

The term alkenyl, wherever used, thus mainly embraces especially uninterrupted and, where appropriate, substituted $C_2$-$C_{22}$alkyl such as vinyl, allyl, etc.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic cyclic moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occurring are heterocyclic aliphatic rings usually containing 5 to 7 ring members, among them at least 1, especially 1-3, heteromoieties, usually selected from O, S, NR10, where R10 is as explained above for interrupting NR10-groups; examples include $C_4$-$C_{18}$cycloalkyl, which is interrupted by S, O, or NR10, such as piperidyl, tetrahydrofuranyl, piperazinyl and morpholinyl. Unsaturated variants may be derived from these structures by abstraction of a hydrogen atom on 2 adjacent ring members with formation of a double bond between them; an example for such a moiety is cyclohexenyl.

Alkoxy such as $C_1$-$C_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

Silyl such as SiRR'R" is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —$SiH(R_2)$ with $R_2$ preferably being hydrocarbyl or hydrocarbyloxy. Preferred hydrocarbyl(oxy) are $C_1$-$C_{20}$alkyl(oxy), aryl(oxy) such as phenyl(oxy), $C_1$-$C_9$alkylphenyl(oxy), where "(oxy)" stands for the optional linker "—O—" which may be present or not. More preferred are three $C_1$-$C_{20}$-alkyl or -alkoxy substituents, i.e. substituted silyl then is $Si(R12)_3$ with R12 being $C_1$-$C_{20}$-alkyl or -alkoxy, especially three $C_1$-$C_8$-alkyl substitutents, such as methyl, ethyl, isopropyl, t-butyl or isobutyl.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) may optionally be located a hole-injecting/transport layer (b), and adjacent to the cathode layer (e) may optionally be located an electron-injection/transport layer (d). Layers (b) and (d) are examples of charge transport layers.

The present complex salts are preferably used as emitters in electroluminescent applications. They are, however, also useful as ionic liquids and/or electrolytes/conductors, e.g. in electrochemical power sources such as photovoltaic devices, electrochemical cells, and batteries, wherein they may replace or supplement the ionic liquids or electrolyte materials conventionally used therein.

The active layer (c) preferably comprises at least approximately 1 weight percent of luminiscent metal complex salt of the present invention.

In some embodiments, the active layer (c) may be substantially 100% of the present metal complex salt because a host charge transporting material, such as $Alq_3$ is not needed. By "substantially 100%" it is meant that the metal complex is the only material in the layer, with the possible exception of impurities or adventitious by-products from the process to form the salt and/or the layer. Still, in some embodiments, the present metal complex salt may be a dopant within a host material, which is typically used to aid charge transport within the active layer (c). The active layer (c) may include an additional other luminescent material, for example a luminescent metal complex, especially a phosphorescent one (i.e. a triplett emitter), which can be a small molecule active material and/or a polymer.

The device may include a support or substrate adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process, inject or gravure printing process. Chemical vapor deposition may be performed as a plasma-enhanced chemical vapor deposition ("PECVD") or metal organic chemical vapor deposition ("MOCVD").

Physical vapor deposition can include all forms of sputtering (e. g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent to the anode. Both hole transporting small molecule compounds and polymers can be used.

Commonly used hole transporting molecules include: N,N'-diphenyl-N,N'-bis(3-methylphenyl)-[1,1'-biphenyl]-4, 4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), N,N'-Di(naphthalen-1-yl)-N,N'-diphenyl-benzidine (NPD), 1,3-bis(9-carbazolyl)benzene (mCP), porphyrinic compounds, and combinations thereof.

Commonly used hole transporting polymers are polyvinylcarbazole, (phenylmethyl) polysilane, poly(3,4-ethylendioxythiophene) (PEDOT), polypyrrole, and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical or physical vapor deposition.

Usually, the anode layer (a) and the hole-injection/transport layer (b), if present, are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction. Layer (b) can be crosslinked.

The active layer (c) comprises the luminescent complex salt of the present invention. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material comprising the present salt is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the copolymers of the present invention. Examples of fluorescent emissive materials include DCM and DMQA. Examples of host materials include $Alq_3$, CBP and mCP. Examples of emissive and host materials are disclosed in U.S. Pat. No. 6,303,238 B, which is incorporated by reference in its entirety.

Examples of methods for forming the active layer (c) include deposition by solution processing. Examples of film-forming methods from a solution include application methods, such as spin-coating, casting, microgravure coating, roll-coating, wire bar-coating, dip-coating, spray-coating, screen-printing, flexography, offset-printing, gravure printing and ink-jet-printing.

As the composition used for forming the active layer (c) at least one kind of present complex salt and at least one solvent are contained, and additives, such as hole transport material, electron transport material, luminescent material, rheology modifier or stabilizer, may be added. The amount of solvent in the composition is 1 to 99 wt % of the total weight of the composition and preferably 60 to 99 wt % and more preferably 80 to 99 wt %.

The solvent used in the solution processing method is not particularly limited and preferably is selected from those able to dissolve or uniformly disperse the materials. Preferably the materials may be dissolved in a solvent, the solution deposited onto a substrate, and the solvent removed to leave a solid film. Any suitable solvents may be used to dissolve the ionic compounds, provided it is inert, may dissolve at least some material and may be removed from the substrate by conventional drying means (e.g. application of heat, reduced pressure, airflow, etc.). Suitable organic solvents include, but are not limited to, are aromatic or aliphatic hydrocarbons, halogenated such as chlorinated hydrocarbons, esters, ethers, ketones, amide, such as chloroform, dichloroethane, tetrahydrofuran, toluene, xylene, ethyl acetate, butyl acetate, methyl ethyl ketone, acetone, dimethyl formamide, dichlorobenzene, chlorobenzene, propylene glycol monomethyl ether acetate (PGMEA), and alcohols, and mixtures thereof. Also water and mixtures with water miscible solvents are possible. Layer (c) may be crosslinked.

Optional layer (d) can function both to facilitate electron injection/transport, hole blocking, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-chelated oxinoid compounds (e. g., tris(8-hydroxyquinolato)aluminum ($Alq_3$) or the like); phenanthroline-based compounds (e. g., 2,9-dimethyl-4,7-diphenyl-1,10-phenanthroline ("DDPA"), 4,7-diphenyl-1,10-phenanthroline ("DPA"), or the like; azole compounds (e. g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like. Layer (d) may be crosslinked.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e. g., Li, Na, K, Rb, Cs), the Group 2 (alkaline earth) metals, the Group 12 metals, the rare earths, the lanthanides (e. g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer(s) may be present within organic electronic devices. For example, a layer between the hole injecting layer (b) and the active layer (c) may facilitate positive charge transport, band-gap matching of the layers, function as a protective layer, or the like. Similarly, additional layers between the electron injecting layer (d) and the cathode layer (e) may facilitate negative charge transport, band-gap matching between the layers, function as a protective layer, or the like. Layers that are known in the art generally may be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The materials of the charge transport layers (b) and (d) often are of the same type as the materials of the active layer (c). More specifically, if the active layer (c) comprises a small molecule compound, then the charge transport layers (b) and (d), if either or both are present, often comprises a different small molecule compound. If the active layer (c) contains a polymer, the charge transport layers (b) and (d), if either or both are present, often contain a polymer, too. Still, the active layer (c) may contain a small molecule compound, and any of its adjacent layers (e.g. charge transport layers) may be polymers.

Each functional layer may be made up of more than one layer. For example, the cathode layer may comprise a layer of a Group I metal and a layer of aluminum. The Group I metal may lie closer to the active layer (c), and the aluminum may help to protect the Group I metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

The electroluminescent devices may be employed for full color display panels in, for example, mobile phones, televisions and personal computer screens. Accordingly the present invention relates also to a device selected from stationary and mobile displays, such as displays for computers, mobile phones, laptops, pdas, TV sets, displays in printers, kitchen equipment, billboards, lightings, information boards and destination boards in trains and buses, containing an organic light emitting diode according to the present invention.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

The compound does not need to be in a solid matrix diluent (e. g., host charge transport material) when used in layer (b) (c), or (d) in order to be effective. A layer greater than approximately 1% by weight of the metal complex compound, based on the total weight of the layer, and up to substantially 100% of the present complex compound can be used as the active layer (c). Additional materials can be present in the active layer (c) with the complex compound. For example, a fluorescent dye may be present to alter the color of emission.

A diluent may also be added. The diluent can be a polymeric material, such as poly (N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

A very promising alternative to OLED particularly for lighting applications is the light-emitting electrochemical cell (LEEC). A LEEC does not need a low-workfunction metal electrode and thicker electroactive layers can be used, while keeping the operating voltage low. The operating mechanism is based on the presence of ions of certain mobility. Thus, upon application of a voltage, the cations and anions move towards the cathode and anode respectively, leading to large electric field gradients at the electrode interfaces. The ion distribution formed facilitates injection of electrons and holes at the cathode and the anode respectively, thus allowing transport and recombination of the charge carriers, which results in emission of a photon. Since the electric field over the electroactive layer is almost completely compensated at the electrode interfaces due to the ion distribution, charge injection is facilitated, even for thick layers. Moreover, matching of the Fermi levels of the electrodes with the energy levels of the electroactive layer is not needed, so that a variety of electrode materials can be used. For instance, non-reactive materials as Au, Ag, Al or ITO can be used as cathode instead of Ba or Ca.

The electroluminescent material may further comprise a substance selected from the group consisting of polyacrylates, polymethacrylates, polyethers, polyesters, polyolefines, polystyrenes, polysiloxanes or mixtures or mixtures or derivatives thereof. For example, the electroluminescent material may comprise polymethylmethacrylate (PMMA). Thereby, film formation is improved resulting in less leakage current and therefore higher efficiency.

The electrode of the LEEC may comprise a material selected from the group consisting of Au, Ag, Al, Pt, Cu, Zn, Ni, Fe, Pb, In, W, Pd, indium tin oxide (ITO), indium zinc oxide, lead oxide, tin oxide, graphite, doped silicon, doped germanium, doped gallium arsenide, doped polyalinine, doped polypyrrole, doped polythiophene, and derivatives and mixtures thereof. These materials are non-reactive and therefore very advantageous to use as electrodes. Further, the present invention relates to a method for manufacturing a light-emitting electrochemical cell comprising arranging an electroluminescent material between at least two electrodes, wherein said electroluminescent material comprises a charged metal complex salt as described above and in the below examples.

The term "light-emitting electrochemical cell" as used herein refers to a device comprising at least two electrodes, inbetween which is placed a material or blend of materials capable of electroluminescence, where this material or a material in the blend of materials is ionic in nature. Suitable materials for use as an electrode according to the invention are e.g. Au, Ag, Al, Pt, Cu, Zn, Ni, Fe, Pb, In, W, Pd, indium tin oxide (ITO), indium zinc oxide, lead oxide, tin oxide, graphite, doped silicon, doped germanium, doped gallium arsenide, doped polyalinine, doped polypyrrole, doped polythiophene, and derivatives and mixtures thereof. Other suitable electrode materials are well known to a man skilled in the art. In addition, alloys of the previously mentioned materials may be used as an electrode according to the present invention.

Both electrodes can in principle be the cathode or the anode. The cathode is defined as the electron-injecting electrode, while the anode is the hole-injecting electrode. The term "anode" as used herein refers to an electrically conductive layer, which is used as electrode for hole injection into the electroluminescent material under appropriate biasing conditions.

An anode according to the invention may be structured, e.g. segmented into separately addressable pixels or connected in series or parallel or intact, possibly with additional thick metal strips for uniform shunting of the currents over large areas. The term "cathode" as used herein refers to an electrically conductive layer, which is used as electrode for electron injection into the electroluminescent material under appropriate biasing conditions.

A cathode according to the invention may be structured or intact, e.g. segmented into separately addressable pixels, or connected in series or parallel or intact, possibly with additional thick metal strips for uniform shunting of the currents over large areas.

In a LEEC according to the invention the electroluminescent material is arranged between an anode and a cathode. By the term "arranged between", in this context, is meant that the electroluminescent material is electrically in contact with the anode and the cathode in such a way that holes and electrons can be introduced into the electroluminescent material and electroluminescence is achieved, under appropriate biasing conditions. For example, the electroluminescent material may be sandwiched between two electrode layers. In another embodiment, the electroluminescent material may be deposited on top of a substrate with predefined anode and cathode electrodes, which are spatially and electrically separated from each other, to form a lateral LEEC.

In yet another embodiment both anode and cathode material may be deposited, with a spatial and electrical separation from each other, on top of the electroluminescent material, thus resulting in a lateral LEEC.

According to the present invention, the electroluminescent material may be mixed with e.g. polymethylmethacrylate, PMMA, in order to improve film formation. Other polymethacrylates could also be added to the electroluminescent material, as well as polyacrylates, polyethers, such as polyethylene oxide or polyethylene glycol, polyesters such as polycarbonates, polyolefines such as Zeonex™, polystyrenes, polysiloxanes or mixtures or derivatives thereof.

The thickness of the electroluminescent material arranged between the electrodes in a LEEC of the invention may vary. For example, the thickness may be in the range of 5 nm to 1 cm, or in the range of 5 nm to 1 mm, or in the range of 10 nm to 0.1 mm.

In the method for manufacturing a LEEC according to the invention, the LEEC may be manufactured on a glass substrate. Suitable substrates may be rigid or mechanically flexible and include, beside glass, metals, alloys and plastics. Examples of flexible substrates include PET foil glued temporarily on a carrier substrate, flexible steel foils, silicon, and silicon oxide.

The invention thus provides an organic electronic device, especially organic light emitting diode or light emitting cell, comprising an emitting layer wherein the emitting layer comprises a complex salt of the invention according to any of the specifications given further above. A preferred device further comprises a hole transport material, especially selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl] 4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde-diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, (phenylmethyl) polysilane, poly(3,4-ethylendioxythiophene) (PEDOT), polyaniline, and combinations thereof, or one or more of the above components doped into a polymer such as polystyrene, polycarbonate.

Devices comprising one or more components of the invention may be stationary and mobile displays, such as displays for computers, mobile phones, laptops, pdas, TV sets, displays in printers, kitchen equipment, billboards, lightings, information boards and destination boards for example in trains and buses, containing an organic light emitting diode or light emitting cell as described above.

A further subject of the invention is a method for the preparation of a light emitting device, which method comprises providing an organic substance layer containing a complex salt according to the invention. An especially advantageous aspect of the invention is the facilitated preparation of white or nearly white light emitting devices by combining appropriate anions and cations in the present salt. The invention thus extends to a method for the preparation of a light emitting device, especially an organic light emitting diode or light emitting cell, wherein a fraction or all light emission is white light, which method comprises providing an organic substance layer containing a complex salt between a pair of electrodes on a substrate, where the salt contains ions whose light emissions essentially are of complementary colour.

The present complex salts may be used in applications other than electronic devices. For example, they may be used as catalysts or indicators (e. g., sensors, oxygen-sensitive indicators, phosphorescent indicators in bioassays, or the like).

The metal complexes of the present invention are conveniently prepared by combining equivalent amounts of the educt complexes comprising a cyclometallated complex anion of a metal M and a simple (i.e. non-complex, organic or inorganic) cation Ka$^+$, and a cyclometallated complex cation of a metal M and a simple (i.e. non-complex, usually inorganic) anion An$^-$, for example of the formulae

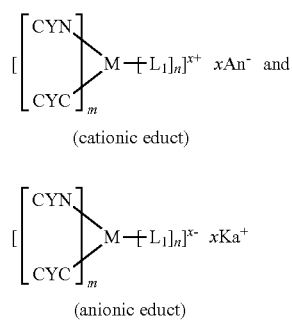

(cationic educt)

(anionic educt)

wherein

An$^-$ is an equivalent of a simple anion, usually of molecular weight from about 17 to about 400 g/mol, for example a halogenide, a carboxylate, sulfate, or a sulfate monoester or phosphate mono- or diester;

Ka$^+$ is an equivalent of a simple cation, usually of molecular weight from 1 to about 400 g/mol, for example an alkaline, ammonium or phosphonium cation;

x usually ranges from 1 to 3;

and M, CYN, CYC, L$_1$, m and n are as defined above, with the proviso that at least one of M, CYN, CYC, L$_1$, especially of CYN, CYC, L$_1$, in the anionic educt is different from its corresponding constituent in the cationic educt, to provide the complex ion charges as indicated.

The combination is preferably done by combining solutions and/or dispersions of both educts using miscible solvents, and essentially removing the simple (i.e. non-complex) ions using suitable methods known in the art (e.g. extraction, dialysis, adsorption using suitable ion exchange materials etc.). Usually, the complex ions dissolve more readily in solvents of lower polarity (such as hydrocarbons, halogenated hydrocarbons etc.) while the simple ions are solvated in more polar solvents (such as water, alcohols etc.).

Isolation of the desired bicomplex product may follow known routes, e.g. removing the solvent under reduced pressure and/or heat and/or using antisolvents inducing precipitation followed by separation of the remaining liquid (e.g. filtration, decantation, centrifugation, drying). The material thus obtainable is of high purity and essentially free of non-complex ions (such as Ka$^+$, An$^-$) and/or water, e.g. containing these ions and/or water at a level below 5% by weight, especially below 1% by weight of the dry product.

The invention thus further provides a process for the preparation of a salt of an organometallic complex cation and an organometallic complex anion as defined further above, which process comprises i) combining equivalent amounts of a compound comprising a cyclometallated complex anion of a metal M and a non-complex organic or inorganic cation with a compound comprising a cyclometallated complex cation of a metal M and a i.e. non-complex inorganic anion, preferably in the form of a solution and/or dispersion, ii) subjecting the combination obtained in step (i) to a technique substantially reducing the concentration of non-complex anions and cations, such as extraction or dialysis using a polar solvent, iii) and, optionally, isolating the complex salt of the invention.

Educt complexes can be prepared according to usual methods known in the art, see e.g. Burrows and Thompson (Appl. Phys. Lett. 1999, 75, 4; Polymer Preprints 2000, 41(1), 770); Allison et al., J. Heterocyclic Chem. 12 (1975) 1275-1277; Nonoyama and Hayata, Transition Met. Chem. 3 (1978) 366-369; US20020055014; US20010019782; Huang et al., Chem. Mater. 16 (2004) 2480-2488; WO06/000544; US2006/0287498; or in the published patent applications (Kokai) JP2005023070, JP2005023071, JP2005023072, JP2005029782, JP2005029783, JP2005029784. In order to modify/adjust charges, analogous processes are carried out using appropriately modified ligands.

A convenient one-step method for preparing iridium metal complexes of formula $Ir(L^a)_3$ ($L^a$ independently being a bidentate ligand such as $L^b$ and/or $L_1$, where $L^b$ is

comprises reacting commercially available iridium trichloride hydrate with an excess of $L^bH$ and/or $L_1$ in the presence of 3 equivalents silver trifluoroacetate and optionally in the presence of a solvent (such as halogen based solvents, alcohol based solvents, ether based solvents, ester based solvents, ketone based solvents, nitrile based solvents, and water). The tris-cyclometallated iridium complexes are isolated and purified by conventional methods. In some cases mixtures of isomers are obtained. Often the mixture can be used without isolating the individual isomers.

The iridium metal complexes of formula $Ir(L^a)_2L_1$ can, for example be prepared by first preparing an intermediate iridium dimer of formula

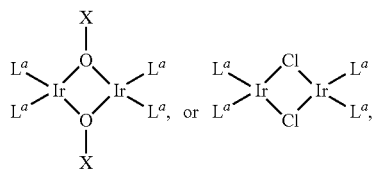

wherein X is H, methyl, or ethyl, and $L^a$ is as defined above, and then addition of $L_1$. The iridium dimers can generally be prepared by first reacting iridium trichloride hydrate with $HL^b$ and/or $L_1$ and adding NaX and by reacting iridium trichloride hydrate with $L_1$ in a suitable solvent, such as 2-ethoxyethanol.

A number of educt complexes/complex salts useful in the preparation are novel compounds, which are obtainable according to methods shown in the examples and/or in analogy to methods known in the art, e.g. as cited. The present invention thus further pertains to a complex of the formula III or IV

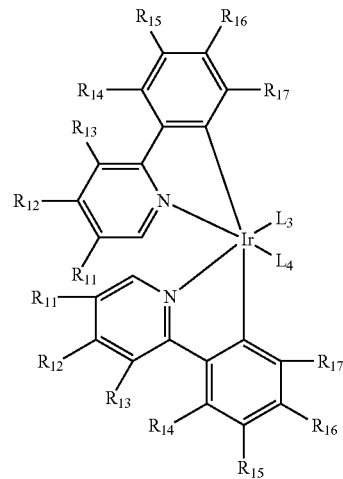

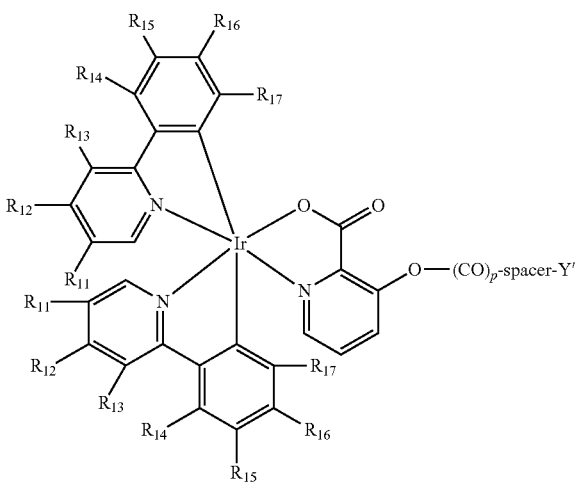

whose charge, if any, is balanced by one or more suitable ions, especially selected from alkali metal cations or halogenide anions; wherein at least one of $R_{11}$, $R_{12}$, $R_{13}$, $R_{14}$, $R_{15}$, $R_{16}$, $R_{17}$ is selected from fluoro, $C_1$-$C_4$alkoxy, phenyl, fluorophenyl, and/or two adjacent residues $R_{11}$ and $R_{12}$, or $R_{12}$ and $R_{13}$, or $R_{13}$ and $R_{14}$, or $R_{14}$ and $R_{15}$, or $R_{15}$ and $R_{16}$, or $R_{16}$ and $R_{17}$ forming, together with the carbon structure they are bonding to, a 6-membered annellated aromatic carbocyclic ring which is unsubstituted or substituted by fluoro, while the other are selected from hydrogen, fluoro, $C_1$-$C_4$alkoxy, phenyl, fluorophenyl;

$L_3$ and $L_4$ are monodentate ligands, or together are one bidentate ligand, as defined for $L_1$ and $L_2$ in claim 7, especially selected from chloro, CN, and bipyridines as of formulae X-34 and X-35;

p is 0 or 1;

spacer is $C_2$-$C_{12}$alkylene or phenylene; and

Y' is OH or an anionic group selected from —COO⁻, —OSO₃⁻.

The following examples are for illustrative purposes only and are not to be construed to limit the instant invention in any manner whatsoever. Room temperature (r.t.) depicts a temperature in the range 20-25° C.; over night denotes a time period in the range 12-16 hours. Percentages are by weight unless otherwise indicated.

Abbreviations used in the examples or elsewhere:
DMF dimethylformamide
THF tetrahydrofuran
DCM dichloromethane
MS mass spectrometry
HRMS high resolution mass spectrometry
ESI electrospray ionization
GC gas chromatography
NMR nuclear magnetic resonance
PMMA poly methylmethacrylate
PVK poly vinylcarbazole
ITO indium tin oxide

EXAMPLES

General Information

All the reactions are carried out under inert atmosphere. All the solvents are used as received from Aldrich or Fluka without further purification. All the following chemicals are used as received: $IrCl_3 \times 3.6H_2O$ (Johnson Matthey), $[Pd(PPh_3)_4]$ (Umicore), sulphur trioxide pyridine complex (≥45% basis on $SO_3$), 2-bromopyridine, 1-chloroisoquinoline, 2-phenylpyridine, bathophenantroline, phenylboronic acid and 2,4-difluoro-phenylboronic acid (Sigma-Aldrich), 3-hydroxypicolinic acid, tetrabutylammonium cyanide, tetrabutylammonium chloride, potassium carbonate anhydrous, sodium carbonate anhydrous, and 2,2'-bipyridil or bpy (Fluka), potassium cyanide (Riedel-de Haën), 6-bromo-hexan-1-ol (TCl).

$^1$H-NMR and $^{19}$F-NMR are recorded by using a Varian Mercury 300 MHz spectrometer and all the deuterated solvents are used as received from suppliers. All the CV measurements are carried out in glove box, by using an AUTOLAB Potentiostat-Galvanostat PGSTAT 302 and all the data are processed with AUTOLAB GPES software. Glassy Carbon (GC) and Platinum wire are used as working and reference electrode respectively, and tetrabutylammonium esafluorophosphate is used as support electrolyte. The redox couple $Fc^{+/0}$ (where Fc is ferrocene) is used as internal standard.

Synthesis of 2-(2,4-difluorophenyl)-pyridine [100]

Scheme 1: Synthesis of [100]

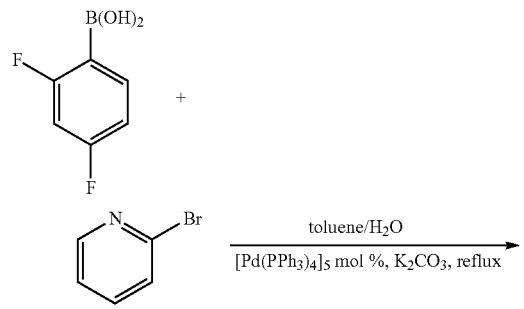

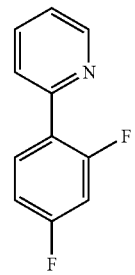

The 2-(2,4-difluorophenyl)-pyridine, hereafter dfppy, is prepared according to the literature procedure, by using the standard condition for the Suzuki-Miyaura cross-coupling reaction (O. Lohse, P. Thevenin and E. Waldvogel, *Synlett*, 1998, 1, 45-48; Scheme 1).

In a typical synthesis, 2-bromopyridine (2.16 mL, 22.12 mmol) and $[Pd(PPh_3)_4]$ (1314.4 mg, 5 mol %) are dissolved in 108 mL of toluene, then a solution of $K_2CO_3$ (11.32 g, 81.90 mmol) in distilled $H_2O$ (18 mL) is added. The resulting biphasic yellow mixture is carefully deoxygenated by $N_2$ bubbling. To the reaction mixture, 2,4-difluoro-phenylboronic acid is added (4191.3 mg, 26.54 mmol, 1.2 eq.). The reaction mixture is refluxed for 18 h at 110° C. under $N_2$. After cooling, at the orange biphasic mixture 60 mL of ter-butyl-methylether are added and the water layer eliminated. The organic layer is washed with 3×150 mL of distilled $H_2O$, and 150 mL of brine, then dried with $Na_2SO_4$ and filtered. The solvents are evaporated until brown-orange oil is obtained. The wished greenish oil-like coupling product is obtained by purification on silica gel column chromatography ($CH_2Cl_2$:AcOEt 95:5), dried and weighted (1961.9 mg, yield 46.4%).

$^1$H-NMR (300 MHz, $CD_2Cl_2$, δ): 6.80-6.98 ppm (2H, m), 7.17 ppm (1H, m) 7.67 ppm (2H, m), 7.95 ppm (1H, m), 8.60 ppm (1H, dt). $^{19}$F-NMR (300 MHz, $CD_2Cl_2$,): −88.07 ppm, −90.89 ppm Synthesis of 2-phenyl-isoquinoline [101]

Scheme 2: Synthesis of [101]

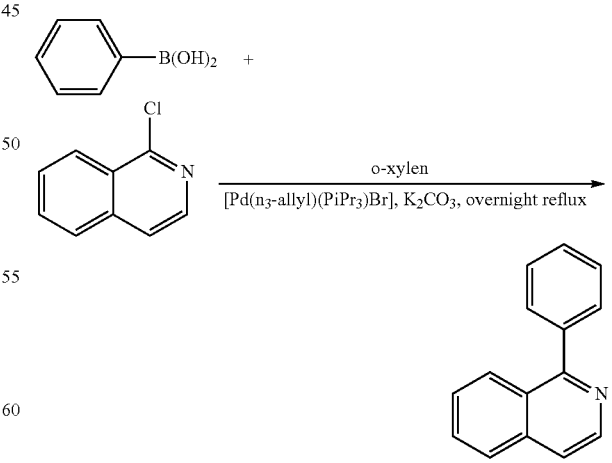

The 2-phenyl-isoquinoline, hereafter piq, is prepared according to the literature procedure, by using the standard condition for the Suzuki-Miyaura cross-coupling reaction (Scheme 2).

In a typical synthesis, 1-chloroisoquinoline (3222.9 mg, 19.7 mmol) and [Pd(η$^3$-allyl)(PiPr$_3$)Br] (372.9 mg, 5 mol %) are dissolved in 75 mL of o-xylen, then K$_2$CO$_3$ (5.45 g, 39.40 mmol) and 1.5 equivalents of phenyl-boronic acid (3602.5 mg, 29.55 mmol) are added. The resulting mixture is carefully deoxygenated by N$_2$ bubbling for 30 min, then it is refluxed for 18 h at 150° C. under Ar. After cooling, at the dark solution 60 mL of ter-butyl-methylether are added. The organic layer is washed with 2×150 mL of distilled H$_2$O, then dried with Na$_2$SO$_4$ and filtered, obtaining an almost colourless solution. The solvents are evaporated until brown oil is obtained. The wished coupling product is obtained by purification on silica gel column chromatography (n-hexane:AcOEt 4:1). The desiderate fractions is dried and a white solid is obtained (3551.0 mg, yield 87.8%).

$^1$H-NMR (300 MHz, CDCl$_3$, δ): 7.40-7.49 ppm (4H, m), 7.55-7.65 ppm (4H, m), 7.81 ppm (1H, pd), 8.04 ppm (1H), 8.55 ppm (1H, pd).

Synthesis of mer-[Ir(ppy)$_2$Cl]$_2$ [200]

Scheme 3: Synthesis of [200]

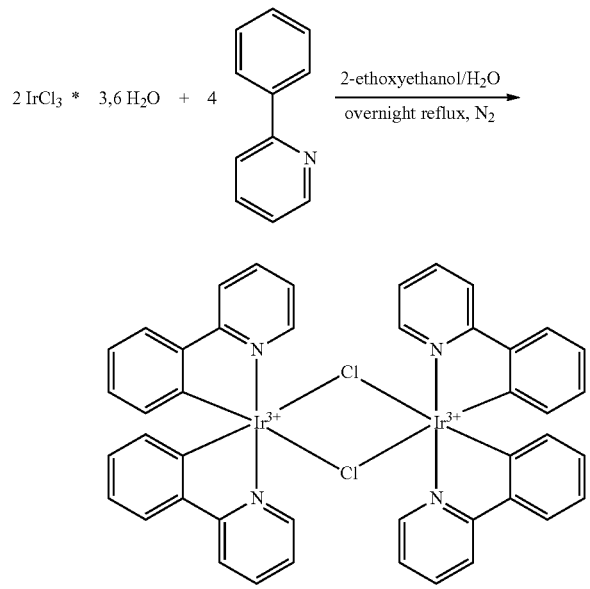

The dimeric chloro-bridged Iridium(III) complex is prepared according to the literature procedure (S. Sprouse, K. A. King, P. J. Spellane, and R. J. Watts, *J. Am. Chem. Soc.*, 1984, 106, 6647-6653; Scheme 3).

In a typical synthesis IrCl$_3$×3.6H$_2$O (2002.3 mg, 5.51 mmol) and 2.5 equivalents of 2-phenylpyridine (ppy, 1.97 mL, 13.76 mmol) are dissolved in 165 mL of a 3:1 v/v mixture of 2-ethoxyethanol and distilled H$_2$O. The resulting mixture is refluxed (120° C.) for 15 hours under nitrogen atmosphere. After cooling, the solution is filtered over a glass frit and the bright yellow solid is carefully washed with 390 mL of absolute EtOH and 390 mL of Et$_2$O. The collected solid is dissolved in 300 mL of CH$_2$Cl$_2$ and the volume of the resulting solution reduced till half. Then, 170 mL of a 3:1 v/v mixture of toluene and n-hexane are added. The mixture is concentrated until few mL and a plentiful bright yellow solid appeared. The solution is removed, the bright yellow solid is washed with 20 mL of n-hexane, then dried and weighted (2685.0 mg, yield 90.9%).

$^1$H-NMR (400 MHz, CDCl$_3$, δ): 5.86 ppm (1H, dd), 6.50 (1H, td), 6.60-6.80 ppm (2H, m), 7.42 ppm (1H, dd), 7.66 ppm (1H, td), 7.80 ppm (1H, dd), 9.17 ppm (1H, dd).

Synthesis of mer-[Ir(dfppy)$_2$Cl]$_2$ [201]

Scheme 4: Synthesis of [201]

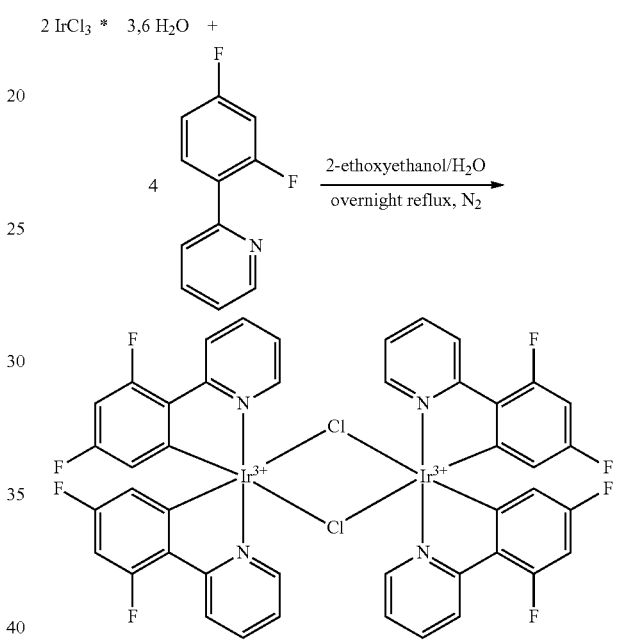

The dimeric chloro-bridged mer-[Ir(dfppy)$_2$Cl]$_2$ complex is prepared according to the literature procedure (S. Sprouse, K. A. King, P. J. Spellane, and R. J. Watts, *J. Am. Chem. Soc.*, 1984, 106, 6647-6653; Scheme 4).

In a typical synthesis IrCl$_3$×3.6H$_2$O (1631.0 mg, 4.46 mmol) and 2.3 equivalents of dfppy [100] (1962.0 mg, 10.26 mmol) are dissolved in 135 mL of a 3:1 v/v mixture of 2-ethoxyethanol and distilled H$_2$O. The resulting mixture is refluxed (120° C.) for 15 hours under nitrogen. After cooling, the solution is filtered over a glass frit and the bright yellow solid is carefully washed with 350 mL of absolute EtOH and 300 mL of Et$_2$O. The collected solid is dissolved in 250 mL of CH$_2$Cl$_2$ and the volume of the resulting solution reduced till half. Then, 170 mL of a 3:1 v/v mixture of toluene and n-hexane is added. The clear mixture is concentrated until few mL and a bright yellow solid appeared. The precipitation is completed with 20 mL of n-hexane then the solid is dried and weighted (2192.0 mg, yield 80.4%).

$^1$H-NMR (300 MHz, CDCl$_3$, δ): 5.22 ppm (1H, dd), 6.25 ppm (1H, m), 6.75 ppm (1H, m), 7.75 (1H), 8.23 ppm (1H), 9.05 ppm (1H). $^{19}$F-NMR (300 MHz, CDCl$_3$,): −86.4 ppm, −88.3 ppm.

Synthesis of mer-[Ir(piq)₂Cl]₂ [202]

Scheme 5: Synthesis of [202]

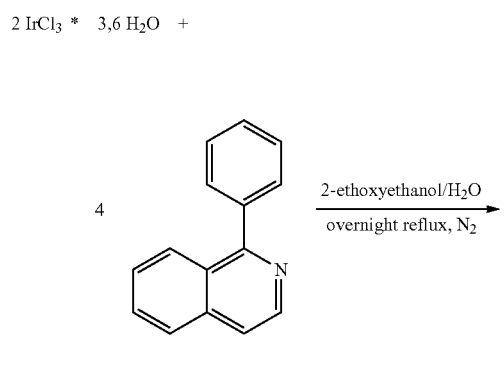

The dimeric chloro-bridged mer-[Ir(piq)₂Cl]₂ complex is prepared according to the literature procedure for similar compounds (S. Sprouse, K. A. King, P. J. Spellane, and R. J. Watts, *J. Am. Chem. Soc.,* 1984, 106, 6647-6653; Scheme 5), where piq is 2-phenyl-isoquinoline [101].

In a typical synthesis IrCl₃×3.6H₂O (2337.0 mg, 6.42 mmol) and 2.3 equivalents of piq [101] (3029.0 mg, 14.76 mmol) are dissolved in 185 mL of a 3:1 v/v mixture of 2-ethoxyethanol and distilled H₂O. The resulting mixture is refluxed (120° C.) for 15 hours under nitrogen. After cooling, the solution is filtered over a glass frit and the orange-red solid is carefully washed with 300 mL of absolute EtOH and 300 mL of Et₂O. The collected solid is dried and weighted (3185.0 mg, yield 77.7%).

$^1$H-NMR (300 MHz, CDCl₃, δ): 5.96 ppm (1H), 6.45 ppm (2H), 6.74 ppm (1H), 7.64-7.73 ppm (1H), 7.74-7.81 ppm (2H), 8.04 ppm (1H), 8.90 ppm (1H), 8.97 ppm (1H).

Synthesis of mer-[Ir(ppy)₂(bpy)]Cl [300]

Scheme 6: Synthesis of [300]

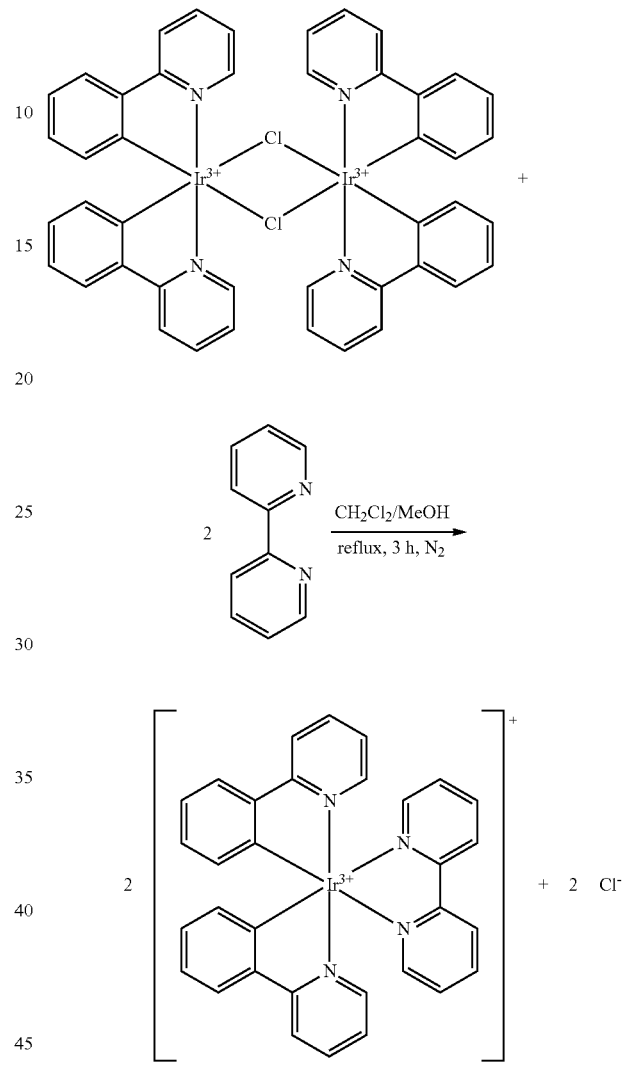

The complex [Ir(ppy)₂(bpy)]Cl is prepared according to the literature procedure, with some modifications in order to obtain the desired chloride salt (O. Lohse, P. Thevenin and E. Waldvogel, *Synlett,* 1998, 1, 45-48; Scheme 6).

In a typical synthesis [Ir(ppy)₂Cl]₂ [200] (1206.4 mg, 1.13 mmol) and 2.2 equivalents of bpy (392.0 mg, 2.51 mmol) are dissolved in 180 mL of a 3:1 v/v mixture of CH₂Cl₂ and MeOH. The resulting mixture is refluxed (60° C.) for 3 hours under nitrogen. After cooling, the solvents are partially removed and 160 mL of a 1:3 v/v mixture of Et₂O and n-hexane are slowly added giving an opaque solution. During the reduction of the volume mixture, the product appeared as yellow solid. Finally [300], it is washed with 30 mL of Et₂O, dried and weighted (1538.0 mg, yield 98.0%).

$^1$H-NMR (300 MHz, CDCl₃, δ): 6.28 ppm (1H, dd), 6.92 ppm (1H, td), 7.03 ppm (2H, m), 7.50 ppm (1H, m), 7.60

(1H), 7.83 ppm (2H, m), 7.98 ppm (1H), 8.07 ppm (1H), 8.13 (1H, td), 8.54 ppm (1H, dd). LC-MS: M+ 657 m/z.

Synthesis of mer-[Ir(dfppy)$_2$(bpy)]Cl [301]

Scheme 7: Synthesis of [301]

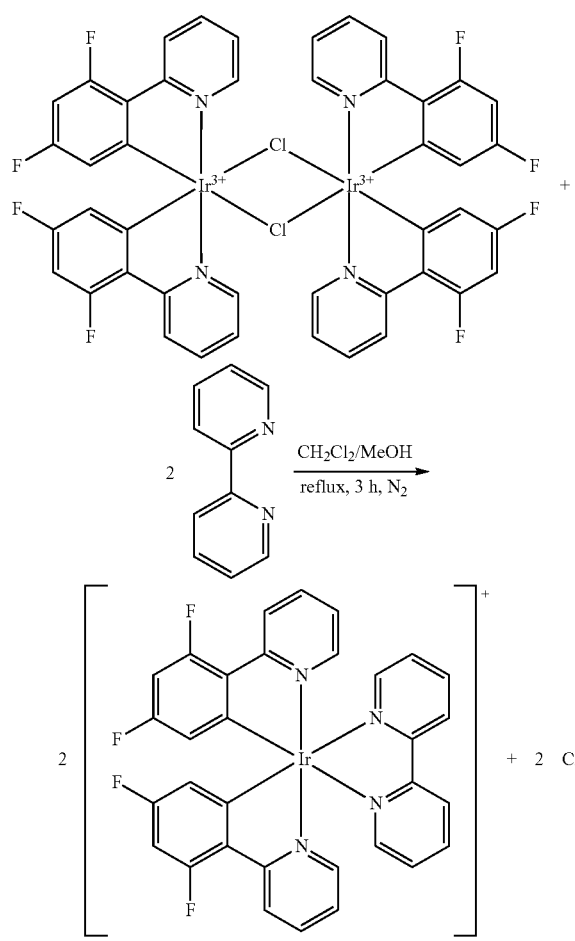

The complex [Ir(dfppy)$_2$(bpy)]Cl is prepared according to the literature procedure, with some modifications in order to obtain the desired chloride salt (Y. Ohsawa, S. Sprouse, K. A. King, M. K. DeArmond, K. W. Hanck, and E. J. Watts, *J. Phys. Chem.* 1987, 91, 1047-1054; E. A. Plummer, J. W. Hofstraad and L. De Cola, *Dalton Trans.* 2003, 2080-2084; Scheme 7).

In a typical synthesis [Ir(dfppy)$_2$Cl]$_2$ [201] (1006.3 mg, 0.82 mmol) and 2.2 eq. of bpy (284.5 mg, 1.81 mmol) are dissolved in 133 mL of a 3:1 v/v mixture of CH$_2$Cl$_2$ and MeOH respectively. The resulting mixture is refluxed (60° C.) for 3 hours under nitrogen. After cooling, the solvents are completely removed and the solid is dissolved in 50 mL of CH$_2$Cl$_2$, then 90 mL of a 3:1 v/v mixture of n-hexane and Et$_2$O are slowly added. The mixture is concentrated until few mL and a bright yellow solid is obtained. The product [301] is washed 3 times with 50 mL of Et$_2$O, dried and weighted (1185.0 mg, yield 93.7%).

$^1$H-NMR (300 MHz, CDCl$_3$, δ): 5.62 ppm (1H, dd), 6.52 ppm (1H, m), 6.97 ppm (1H), 7.39 ppm (2H, m), 7.70-7.85 (2H, m), 8.25 ppm (2H, m), 8.83 ppm (1H). $^{19}$F-NMR (300 MHz, CDCl$_3$,): −84.10 ppm, −86.65 ppm. LC-MS: M+ 729 m/z.

Synthesis of mer-[Ir(ppy)$_2$(bphen)]Cl [302]

Scheme 8: Synthesis of [302]

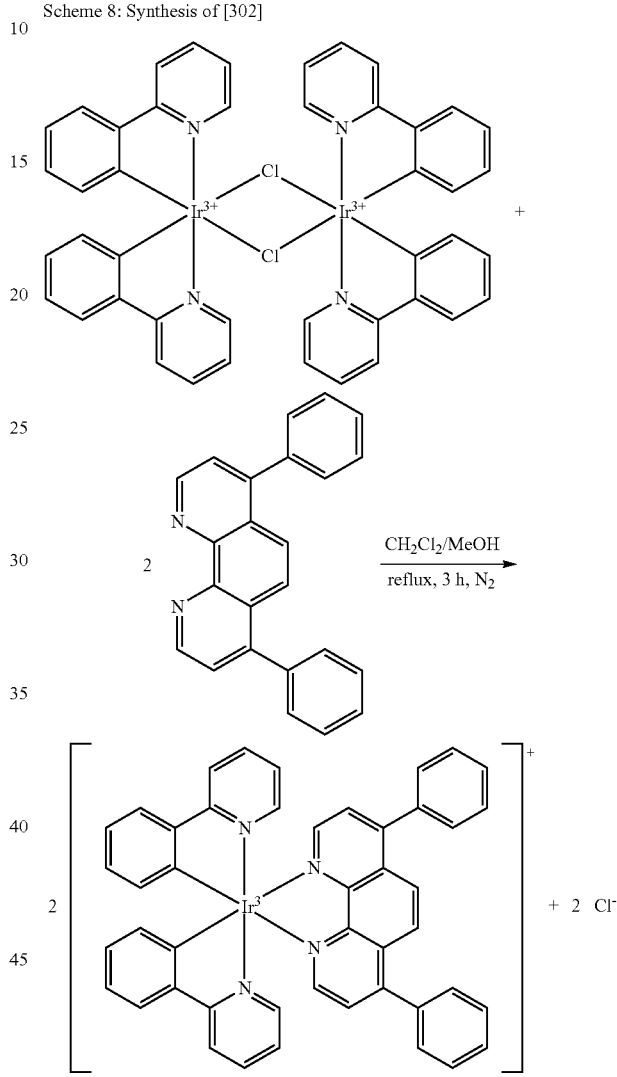

The complex [Ir(ppy)$_2$(bphen)]Cl, where bphen is bathophenantroline or 4,7-diphenyl-1,10-phenanthroline, is prepared according to the literature procedure (H. J. Bolink, L. Cappelli, E. Coronado, M. Grätzel, E. Ortí, R. D. Costa, P. M. Viruela, and Md. K. Nazeeruddin, *J. Am. Chem. Soc.,* 2006, 128, 14786-14787; see Scheme 8), with some modifications in order to obtain the desired chloride salt.

In a typical synthesis [Ir(ppy)$_2$Cl]$_2$ [200] (1003.4 mg, 0.93 mmol) and 2.2 eq. of bphen (688.7 mg, 2.06 mmol) are dissolved in 165 mL of a 3:1 v/v mixture of CH$_2$Cl$_2$ and MeOH respectively. The resulting mixture is refluxed (60° C.) for 3 hours under nitrogen. After cooling, the solvents completely removed, and the orange-red solid is dissolved in 55 mL of CH$_2$Cl$_2$, then 80 mL of a mixture of Et$_2$O and n-hexane in a three-to-one ratio are added. The almost clear solution is concentrated giving an orange-yellow solid [302].

The precipitation is completed with 30 mL of n-hexane, washed 2×50 mL of Et$_2$O, dried and weighted (1569 mg, yield 96.6%).

$^1$H-NMR (300 MHz, CDCl$_3$, δ): 6.37 ppm (1H, dd), 6.91 ppm (1H, td), 7.02 ppm (1H, td), 7.17 ppm (1H, m), 7.52-7.58 ppm (6H, m), 7.67 ppm (2H), 7.76 ppm (1H, td), 7.88 ppm (1H), 8.10 ppm (1H, s), 8.28 ppm (1H, d). LC-MS: M$^+$ 833 m/z.

Synthesis of mer-[Ir(piq)$_2$(bpy)]Cl [303]

Scheme 9: Synthesis of [303]

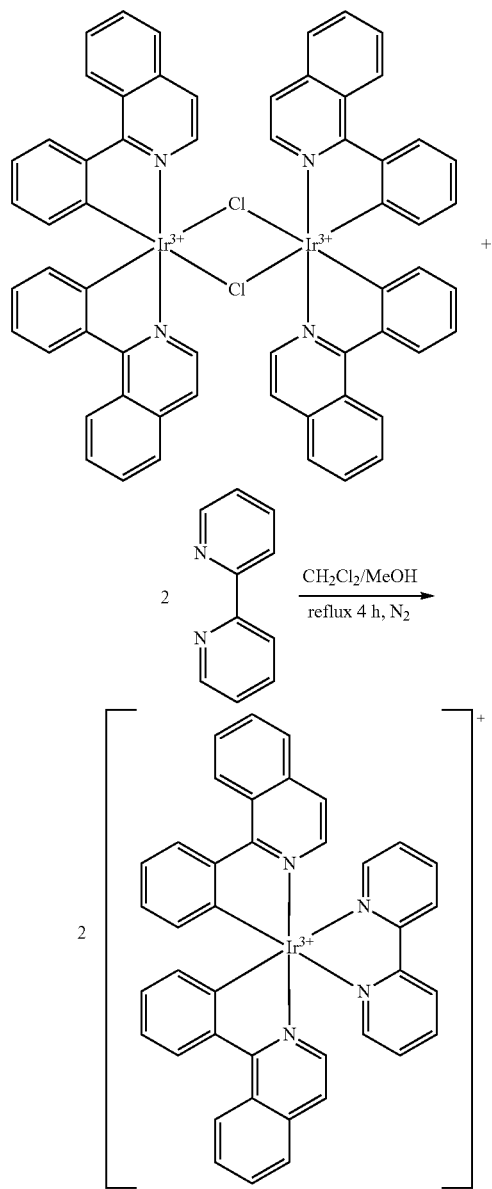

The complex [Ir(piq)$_2$(bpy)]Cl is prepared according to the literature procedure (Y. Ohsawa, S. Sprouse, K. A. King, M. K. DeArmond, K. W. Hanck, and E. J. Watts, *J. Phys. Chem.* 1987, 91, 1047-1054; E. A. Plummer, J. W. Hofstraad and L. De Cola, *Dalton Trans.* 2003, 2080-2084; see Scheme 9), with some modifications in order to obtain the desired chloride salt.

In a typical synthesis [Ir(piq)$_2$Cl]$_2$ [202] (1202.4 mg, 0.94 mmol) and 2.2 eq. of bpy (327.4 mg, 2.10 mmol) are dissolved in 380 mL of a 3:1 v/v mixture of CH$_2$Cl$_2$ and MeOH respectively. The resulting red coloured mixture is refluxed (60° C.) for 24 hours under nitrogen. After cooling, the solvents completely removed and the orange-red solid is dissolved in 50 mL of CH$_2$Cl$_2$, then 70 mL of a 3:1 v/v mixture of n-hexane and Et$_2$O respectively are added. The almost clear solution is concentrated and the product [303] appeared as a plentiful red solid, that is washed 2×50 mL with Et$_2$O, dried and weighted (1420 mg, yield 94.8%)

$^1$H-NMR (300 MHz, CDCl$_3$, δ): 6.23 ppm (1H), 6.82 ppm (1H), 7.04 ppm (1H), 7.22-7.30 ppm (3H, m), 7.63 ppm (1H), 7.71 ppm (2H), 7.83 ppm (1H), 8.21 ppm (2H), 8.86 ppm (1H), 9.73 ppm (1H). LC-MS: M$^+$ 757 m/z.

Synthesis of mer-[Ir(ppy)$_2$(CN)$_2$]$^-$[$^n$-Bu$_4$N]$^+$ [400]

Scheme 10: Synthesis of [400]

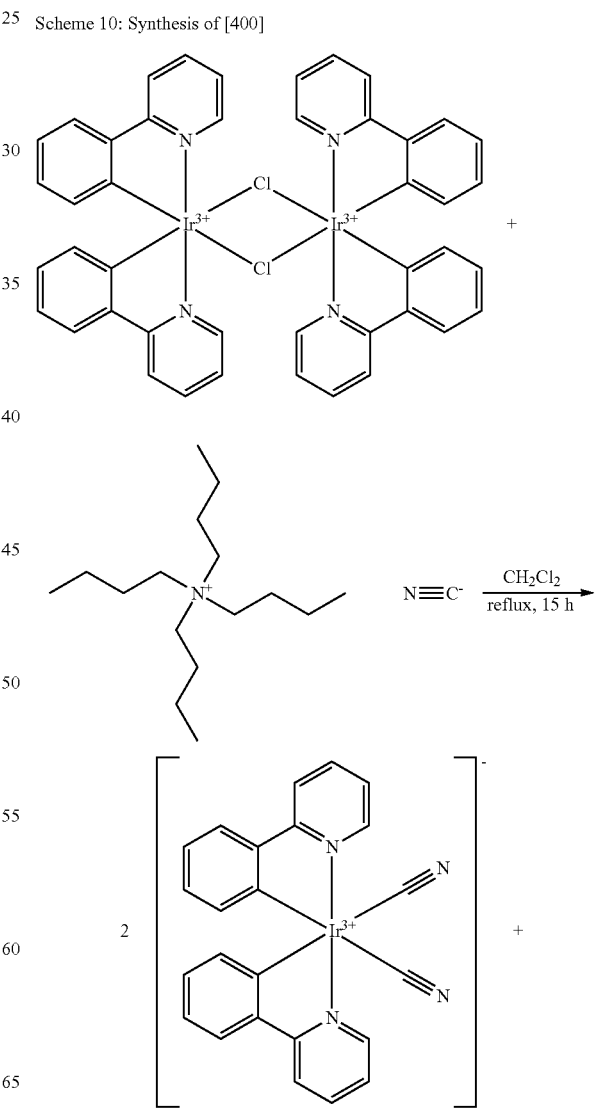

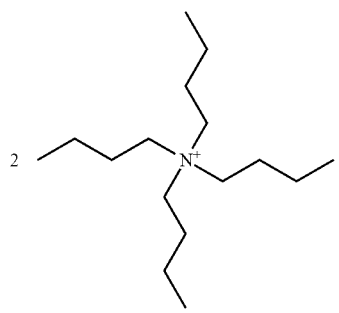

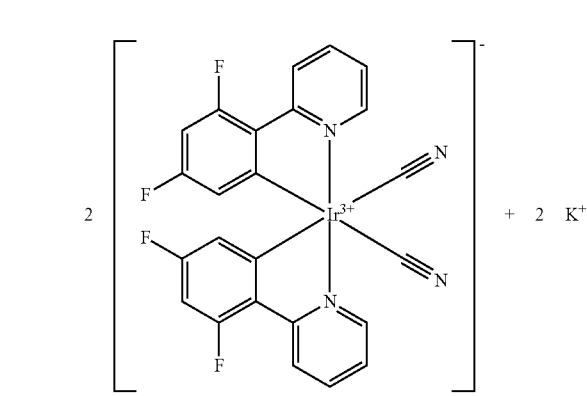

The complex [Ir(ppy)$_2$(CN)$_2$]TBA, where TBA is the tetrabutylammonium ion, is prepared according to the literature procedure, with some modifications (Md. K. Nazeeruddin, R. H. Humphry-Baker, D. Berner, S. Rivier, L. Zuppiroli, and M. Grätzel, *J. Am. Chem. Soc.*, 2003, 125, 8790-8797; D. Di Censo, s. Fantacci, F. De Angelis, C. Klein, N. Evans, K. Kalyanasundaram, H. J. Bolink, M. Grätzel, and M. K. Nazeeruddin, *Inorg. Chem.* 2008, 47, 980-989; Scheme 10).

In a typical synthesis [Ir(ppy)$_2$Cl]$_2$ [202] (2501.9 mg, 2.320 mmol) and 10 equivalents of TBACN (6221.0 mg, 23.21 mmol) are dissolved in 430 mL of CH$_2$Cl$_2$. The resulting greenish-yellow solution is refluxed (50° C.) for 15 hours under nitrogen atmosphere. After cooling, the solution is washed 3×400 mL of distilled H$_2$O in order to remove the excess of TBACN and 200 mL of AcOEt are added to the reaction mixture. The obtained solution is concentrated till few mL and a yellow solid appeared, and is completed with 300 mL of Et$_2$O. The product [400] is washed with 60 mL of Et$_2$O and 2×80 mL of distilled water, dried and weighted (3255.0 mg, yield 88.2%).

$^1$H-NMR (300 MHz, DMSO-d$_6$, δ): 0.92 ppm (6H, t), 1.29 ppm (4H, qt), 1.55 ppm (4H, m), 3.14 ppm (4H, m), 6.07 ppm (1H, dd), 6.59 (1H, td), 6.71 ppm (1H, td), 7.29 ppm (1H, m), 7.64 ppm (1H), 7.87 ppm (1H), 9.52 ppm (1H). LC-MS: M$^+$ 242 m/z (TBA$^+$); M$^-$ 553 m/z [Ir(ppy)$_2$(CN)$_2$]$^-$.

The complex K[Ir(dfppy)$_2$(CN)$_2$] is prepared according to the literature procedure for the similar [Ir(dfppy)$_2$(CN)$_2$] TBA, with appropriated modifications (H. J. Bolink, L. Cappelli, E. Coronado, M. Grätzel, E. Ortí, R. D. Costa, P. M. Viruela, and Md. K. Nazeeruddin, *J. Am. Chem. Soc.*, 2006, 128, 14786-14787; see Scheme 11).

In a typical synthesis [Ir(dfppy)$_2$Cl]$_2$ [201] (1852.8 mg, 1.52 mmol) and 10 eq. of KCN (991.2 mg, 15.22 mmol) are dissolved in 160 mL of a 1:1 v/v mixture of CH$_2$Cl$_2$ and MeOH. The resulting greenish-yellow solution is refluxed (65° C.) for 15 hours under nitrogen atmosphere. After cooling, the solution is completely evaporated. The wished compound is selectively dissolved in 80 mL of acetone, then the solution is filtered over a glass frit, concentrated until the third part of the original volume and 110 mL of a 10:1 v/v mixture of n-hexane and Et$_2$O, then 30 mL of n-hexane are used for the precipitation. The pale yellow-green solid [401] is dried and weighted (1.37 g, yield 67.9%).

$^1$H-NMR (300 MHz, acetone-d$_6$, δ): 5.60 ppm (1H, pdd), 6.22 ppm (1H, ptd), 7.18 ppm (1H, pt), 7.84 ppm (1H, pt), 8.11 (1H, pd), 9.68 ppm (1H, pd). $^{19}$F-NMR (300 MHz, acetone-d$_6$,): −89.48 ppm, −90.30 ppm. LC-MS: M$^+$ 625 m/z.

Synthesis of mer-[Ir(dfppy)$_2$(CN)$_2$]K [401]

Scheme 11: Synthesis of [401]

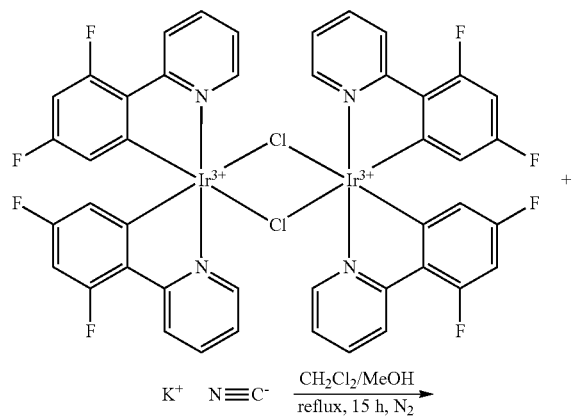

Synthesis of [Ir(ppy)$_2$(CN)$_2$]$^-$[Ir(ppy)$_2$(bpy)]$^+$ [500]

Scheme 12: Synthesis of [500]

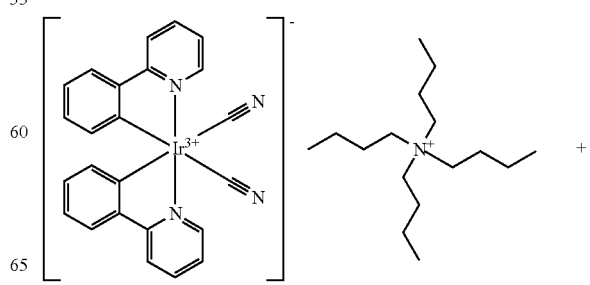

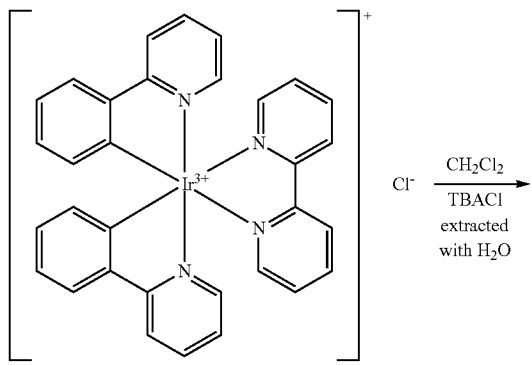

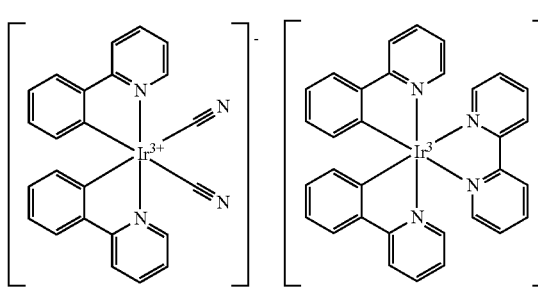

The double complex salt [Ir(ppy)$_2$(CN)$_2$]$^-$[Ir(ppy)$_2$(bpy)]$^+$ is prepared from a strictly equimolar CH$_2$Cl$_2$ solution of the two starting complexes in the following way (see also Scheme 12).

The complexes [Ir(ppy)$_2$(CN)$_2$]TBA [400] (1268.3 mg, 1.59 mmol) and [Ir(ppy)$_2$(bpy)]Cl [300] (1101.0 mg, 1.59 mmol) are dissolved together in 500 mL of CH$_2$Cl$_2$. In order to remove the TBACl, the resulting solution is washed 8 times with 600 mL of distilled H$_2$O. The volume of the organic layer is reduced and 150 mL of a 3:1 v/v mixture of Et$_2$O and n-hexane are used to precipitate a yellow solid [500]. The obtained solid is dissolved in CH$_2$Cl$_2$ and precipitated again with a 1:1 v/v mixture of Et$_2$O and n-hexane, then dried and weighted (1523.0 mg, yield 79.0%).

$^1$H-NMR (300 MHz, CD$_2$Cl$_2$, δ): 6.20 ppm (2H), 6.64 ppm (1H, td), 6.73 ppm (1H, td), 6.88 ppm (2H, m), 6.99 ppm (2H, m), 7.32 ppm (1H, td), 7.41 ppm (1H, dd), 7.50 ppm (1H, dd), 7.60-7.80 ppm (4H, m), 7.87 ppm (2H), 8.06 ppm (1H, td), 8.79 ppm (1H, d), 9.59 ppm (1H, d). LC-MS: M$^+$ 657 m/z; M$^-$ 553 m/z. HR-MS: [Ir(ppy)$_2$(bpy)]$^+$, C$_{32}$H$_{24}$IrN$_4$ exact mass 657.1630, measured mass 657.1625; [Ir(ppy)$_2$(CN)$_2$]$^-$, C$_{24}$H$_{16}$IrN$_4$ exact mass 553.1004, measured mass 553.1004. Elemental analysis: found: C, 54.12/53.97%, H, 3.33/3.47%, N, 8.85/8.83%, Ir 32.1%; calcd. C, 55.62%, H, 3.33%, N, 9.27%, Ir 31.78%. CV analysis (scan rate 100 mV/s): oxidation in CH$_2$Cl$_2$ peak: +0.497 V, +0.881 V; reduction in THF peak: −1.817V, −2.717V, −3.144V. Melting point: 264° C.

Synthesis of [Ir(dfppy)$_2$(CN)$_2$]$^-$[Ir(ppy)$_2$(bpy)]$^+$ [501]

Scheme 13: Synthesis of [501]

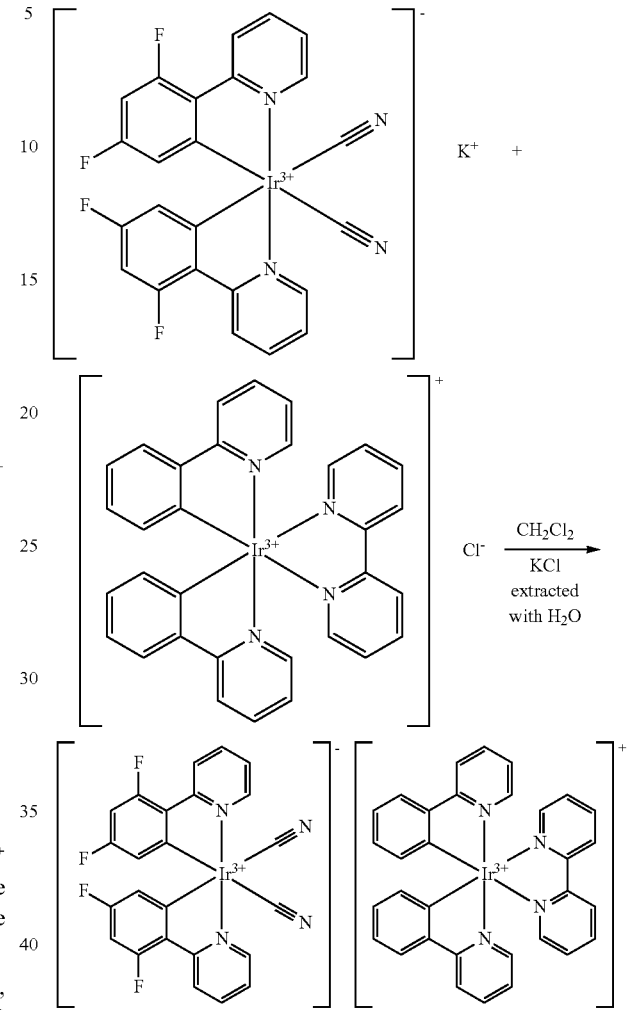

The double complex salt [Ir(dfppy)$_2$(CN)$_2$]$^-$[Ir(ppy)$_2$(bpy)]$^+$ is prepared from a strictly equimolar CH$_2$Cl$_2$ solution of the two starting complexes in the following way (see also Scheme 13).

The complexes K[Ir(dfppy)$_2$(CN)$_2$] [401] (809.4 mg, 1.22 mmol) and [Ir(ppy)$_2$(bpy)]Cl [300] (841.9 mg, 1.22 mmol) are dissolved together in 650 mL of CH$_2$Cl$_2$. In order to remove the KCl, the resulting solution is washed 5 times with 500 mL of distilled H$_2$O. The volume of the organic layer is reduced till ½ of the original one and then 130 mL of a 3:1 v/v mixture of Et$_2$O and n-hexane are used to obtain an opaque solution. The precipitation of the product is achieved by concentration and is completed by adding of 30 mL of n-hexane. The yellow-orange solid [501] is washed with 30 mL of n-hexane, dried and weighted (1299.0 mg, yield 83.0%).

$^1$H-NMR (300 MHz, CD$_2$Cl$_2$, δ): 5.64 ppm (1H, dd), 6.10-6.25 ppm (2H, m), 6.89 ppm (2H, m), 7.00 ppm (2H), 7.38 ppm (2H, m), 7.65 ppm (3H, m), 7.85-7.93 ppm (2H, m), 7.98 ppm (1H, td), 8.15 ppm (1H, m) 8.53 ppm (1H), 9.66 ppm (1H). $^{19}$F-NMR (300 MHz, CD$_2$Cl$_2$,): −88.35 ppm, −89.20 ppm. LC-MS: M$^+$ 657 m/z; M$^-$ 625 m/z. HR-MS: [Ir(ppy)$_2$(bpy)]$^+$, C$_{32}$H$_{24}$IrN$_4$ exact mass 657.1630, measured mass 657.1561; [Ir(dfppy)$_2$(CN)$_2$]$^-$, C$_{24}$H$_{12}$F$_4$IrN$_4$ exact mass 625.0628, measured mass 625.0691. Elemental analysis:

found: C, 52.86/52.48%, H, 3.29/3.32%, N, 8.22/8.23%, F 6.03%, Ir 31.6%; calcd. C, 52.49%, H, 2.83%, N, 8.74%, F 5.93%, Ir 30.00%. CV analysis (scan rate 100 mV/s): oxidation in $CH_2Cl_2$ peak: +0.750 V, +0.880 V; reduction in THF peak: −1.82 V, −2.69 V, −2.97 V. Melting point: 234° C.

Synthesis of $[Ir(ppy)_2(CN)_2]^-[Ir(dfppy)_2(bpy)]^+$ [502]

Scheme 14: Synthesis of [502]

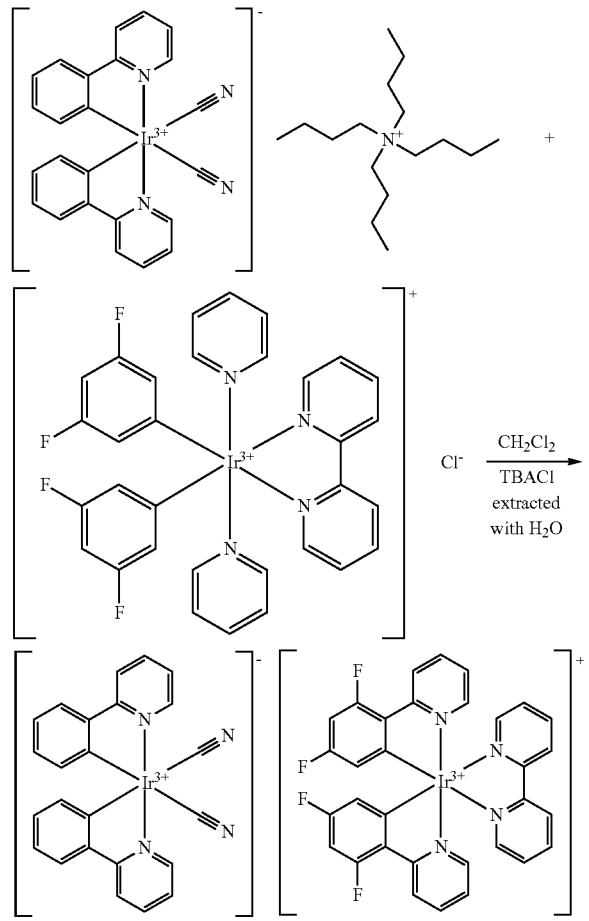

The double complex salt $[Ir(ppy)_2(CN)_2]^-[Ir(dfppy)_2(bpy)]^+$ is prepared from a strictly equimolar $CH_2Cl_2$ solution of the two starting complexes in the following way (see also Scheme 14).

The complexes $[Ir(ppy)_2(CN)_2]$TBA [400] (817.3 mg, 1.03 mmol) and $[Ir(dfppy)_2(bpy)]Cl$ [302] (790.0 mg, 1.03 mmol) are dissolved together in 250 mL of $CH_2Cl_2$. In order to remove the TBACl, the resulting solution is washed 8 times with 600 mL of distilled $H_2O$. At the organic layer 100 mL of a 3:1 v/v mixture of $Et_2O$ and n-hexane are added. The opaque resulting mixture is concentrated and 50 mL of the same $Et_2O$/n-hexane mixture aided to precipitate a yellow solid. The product [502] is re-precipitated again from $CH_2Cl_2$ and 1:1 v/v $Et_2O$ and n-hexane, washed with 50 mL of $Et_2O$, dried and weighted (1142.0 mg, yield 86.3%).

$^1$H-NMR (300 MHz, $CD_2Cl_2$, δ): 5.66 ppm (1H, dd), 6.19 ppm (1H), 6.53 ppm (1H), 6.63 ppm (1H, dt) 6.73 ppm (1H, td), 6.94 ppm (2H, m), 7.39 ppm (2H), 7.50 (1H), 7.61 ppm (1H), 7.72 ppm (2H, m), 7.85 ppm (1H), 8.05 ppm (1H), 8.22 ppm (1H), 8.81 ppm (1H), 9.62 ppm (1H). $^{19}$F-NMR (300 MHz, $CD_2Cl_2$,): −85.25 ppm, −86.95 ppm. LC-MS: M$^+$ 729 m/z; M$^-$ 552 m/z. HR-MS: $[Ir(ppy)_2(bpy)]^+$, $C_{32}H_{20}F_4IrN_4$ exact mass 729.1254, measured mass 729.1221; $[Ir(dfppy)_2(CN)_2]^-$, $C_{24}H_{16}IrN_4$ exact mass 553.1004, measured mass 553.0951. Elemental analysis: found: C, 50.38/50.79%, H, 2.98/2.99%, N, 8.23/8.33%, F 5.84%, Ir 30.8%; calcd. C, 52.49%, H, 2.83%, N, 8.74%, F 5.93%, Ir 30.00%. CV analysis (scan rate 100 mV/s): oxidation in $CH_2Cl_2$ peak: +0.488 V; reduction in THF peak: −1.72 V, −2.60 V, −2.77 V. Melting point: 252° C.

Synthesis of $[Ir(ppy)_2(CN)_2]^-[Ir(ppy)_2(bphen)]^+$ [503]

Scheme 15: Synthesis of [503]

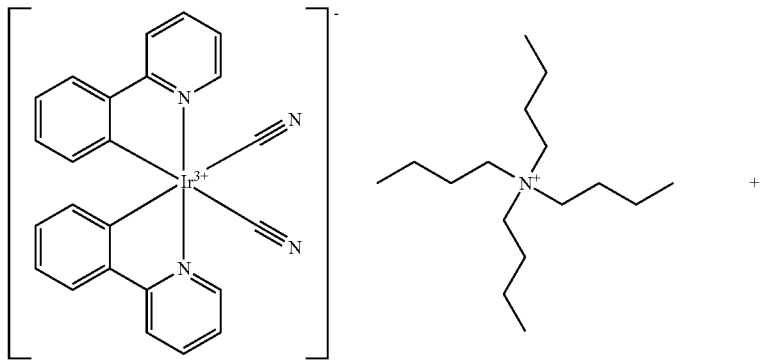

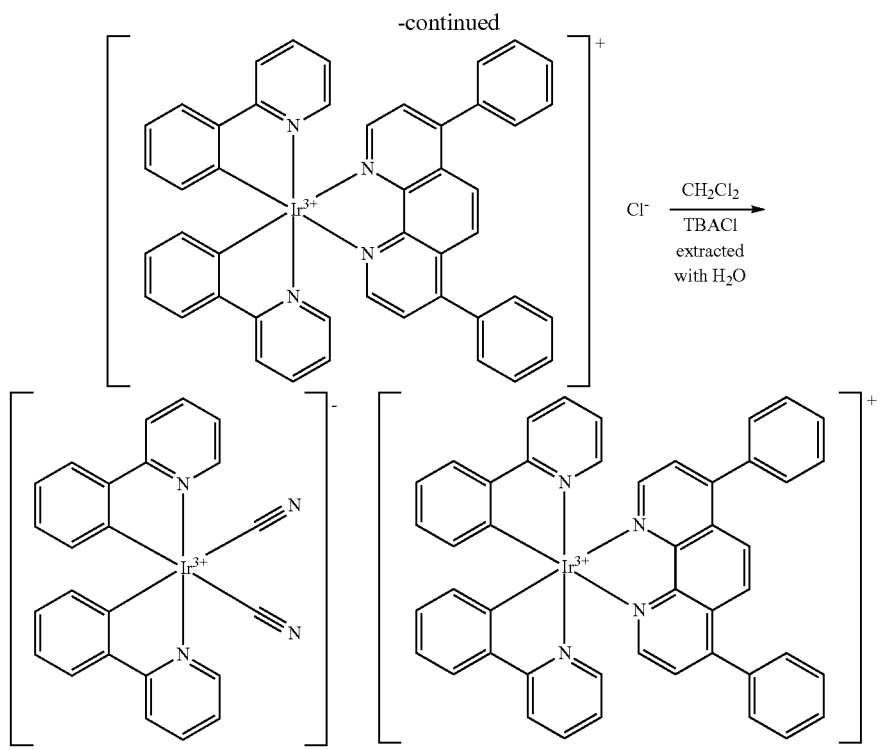

The double complex salt [Ir(ppy)$_2$(CN)$_2$]$^-$[Ir(ppy)$_2$(bphen)]$^+$ is prepared from a strictly equimolar CH$_2$Cl$_2$ solution of the two starting complexes in the following way (see also Scheme 15).

The complexes [Ir(ppy)$_2$(CN)$_2$]TBA [400] (736.6 mg, 0.926 mmol) and [Ir(ppy)$_2$(bphen)]Cl [302] (808.0 mg, 0.926 mmol) are dissolved together in 300 mL of CH$_2$Cl$_2$. In order to remove the TBACl, the resulting solution is washed 8 times with 600 mL of distilled H$_2$O. The volume of the organic layer is reduced and then 120 mL of a 3:1 v/v mixture of Et$_2$O and n-hexane are added. The opaque resulting mixture is concentrated and 80 mL of the same Et$_2$O/n-hexane mixture aided to precipitate an orange-yellow solid. The product [503] is re-precipitated again from CH$_2$Cl$_2$ and 3:1 v/v Et$_2$O and n-hexane, dried and weighted (1131.0 mg, yield 87.7%).

$^1$H-NMR (300 MHz, CD$_2$Cl$_2$, δ): 6.18 ppm (1H, dd), 6.37 ppm (1H), 6.62 ppm (1H, dt), 6.71 ppm (1H, dt) 6.83 ppm (1H), 6.95 ppm (2H, m), 7.06 ppm (1H), 7.40 (1H), 7.45-7.55 ppm (6H, m), 7.57-7.75 ppm (5H, m), 7.91 ppm (1H), 8.09 ppm (1H, s), 8.30 ppm (1H, d), 9.62 ppm (1H). Elemental analysis: found: C, 59.47/59.26%, H, 3.92/3.88%, N, 7.83/7.83%, Ir 28.7%; calcd. C, 60.68%, H, 3.49%, N, 8.09%, Ir 27.74%. CV analysis (scan rate 100 mV/s): oxidation in CH$_2$Cl$_2$ peak: 1 0.51 V, 0.824 V; reduction in THF peak: −1.73 V, −2.53 V, −2.96 V. Melting point: 282° C.

Synthesis of [Ir(ppy)$_2$(3-OH-pic)] [600]

Scheme 16: Synthesis of [600]

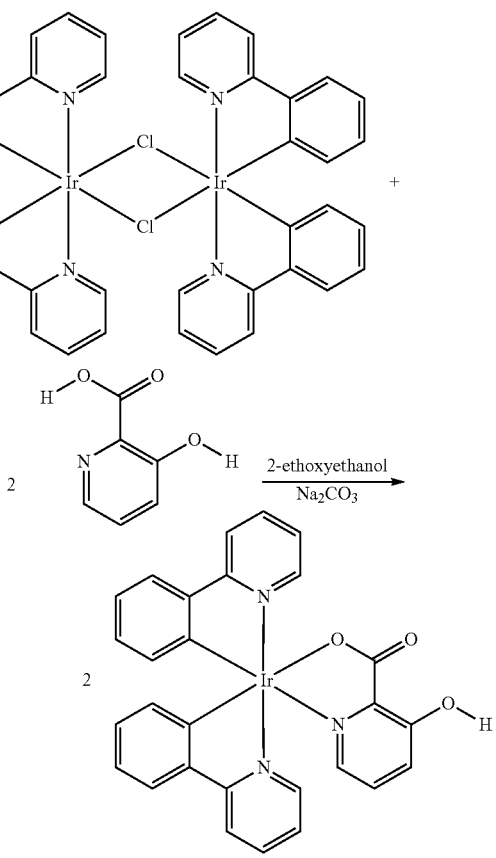

The complex [Ir(ppy)$_2$(3-OH-pic)] is prepared according to the literature procedure (T.-H. Kwon, M. K. Kim, J. Kwon, D.-Y. Shin, S. J. Park, C.-L. Lee, J.-J. Kim, and Jong-In Hong, *Chem. Mater.* 2007, 19, 3673-3680; Scheme 16).

In a typical synthesis [Ir(ppy)$_2$Cl]$_2$ [200] (1515.0 mg, 1.41 mmol), 2.6 equivalents of 3-hydroxypicolinic acid (508.5 mg, 3.65 mmol) and 4.4 equivalents of anhydrous Na$_2$CO$_3$ (656.1 mg, 6.18 mmol) are dissolved in 90 mL of 2-ethoxyethanol. The resulting greenish-yellow solution is heated (135° C.) for 24 hours under nitrogen atmosphere.

After cooling, the solution is filtered over a glass frit (IV) and the solid washed with EtOH and acetone. The filtered solution is concentrated till few mL then 40 mL of Et$_2$O and 50 mL of a 1:1 v/v mixture of Et$_2$O and n-hexane are added. A yellow solid appeared and its precipitation is completed with 120 mL of n-hexane. The yellow solid is separated by filtration, washed with Et$_2$O and dried. The crude product [600] is washed with distilled H$_2$O, filtered again and recrystallized from CH$_2$Cl$_2$ and Et$_2$O/n-hexane, then washed with Et$_2$O, dried and weighted. (1348.3 mg, 74.8% yield).

$^1$H-NMR (300 MHz, DMSO-d$_6$, δ): 6.05 ppm (1H, dd), 6.19 ppm (1H, dd), 6.66-6.76 ppm (2H), 6.79-6.90 ppm (3H), 7.11-7.27 ppm (3H, m), 7.37 ppm (1H), 7.61 ppm (1H, dd), 7.77 ppm (2H), 7.91 ppm (2H), 8.17 ppm (2H), 8.52 ppm (1H, dd) 13.8 ppm (—OH, the integral is less then 1 due the possible H bond with H$_2$O). LC-MS: M$^+$ 639.11 m/z.

Synthesis of [Ir(ppy)$_2$(pic-3-OC$_6$H$_{12}$OH)] [601]

Scheme 17: Synthesis of [601]

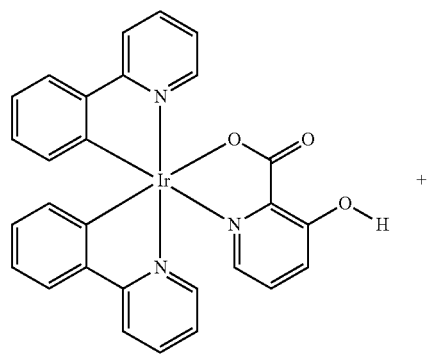

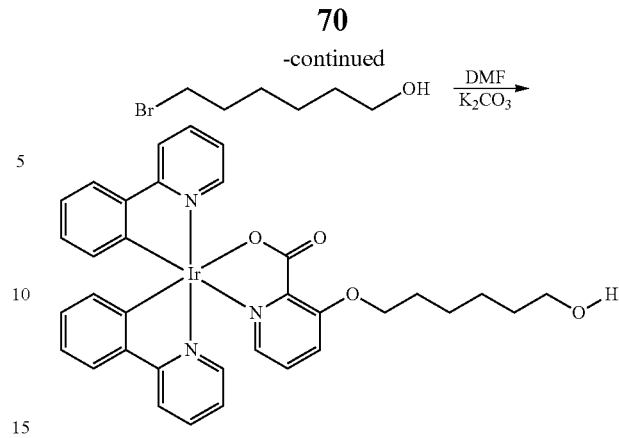

The titled compound is prepared from the 3-hydroxypicolinate Iridium derivative via nucleophilic substitution on the bromine atom in the alkyl halide, as depicted in Scheme 17.

In a typical synthesis [Ir(ppy)$_2$(3-OH-pic)] [600] (1032.6 mg, 1.61 mmol), 2 equivalents of 6-bromo-hexan-1-ol (425 L, 3.25 mmol) and 3 equivalents of anhydrous K$_2$CO$_3$ (670.4 mg, 4.85 mmol) are dissolved in 13 mL of dry DMF. The resulting suspension is stirred and heated at 90° C. The reaction is followed by TLC (AcOEt:CH$_2$Cl$_2$:MeOH 7:7:3). After 48 h, 150 mL of CH$_2$Cl$_2$ are added and the resulting mixture washed with 150 mL of an watery buffer at pH 7, then 2×150 mL of distilled H$_2$O. The organic phase is dried with Na$_2$SO$_4$ and the solvents evaporated. The orange oil obtained is purified on silica gel column chromatography (AcOEt:CH$_2$Cl$_2$:MeOH 7:7:3). The desiderated fractions are collected and the solvents completely evaporated, giving a yellow solid [601] that is dried and weighted (530 mg, yield 44.4%).

$^1$H-NMR (300 MHz, DMSO-d$_6$, δ): 1.30-1.46 ppm (6H, m, —CH$_2$—CH$_2$—CH$_2$—CH$_2$—CH$_2$—), 1.73 ppm (2H, —CH$_2$—CH$_2$—OH), 3.38 ppm (2H, t, —CH$_2$—CH$_2$—OH), 4.06 ppm (2H, t, pic-3O—CH$_2$—), 6.01 ppm (1H, dd), 6.20 ppm (1H, dd), 6.64-6.78 ppm (2H), 6.80-6.90 ppm (2H, dt), 7.22 ppm (2H, td), 7.37 ppm (1H, m), 7.45 ppm (1H), 7.57 (1H), 7.75 ppm (3H), 7.91 ppm (2H, m), 8.18 ppm (2H), 8.55 ppm (1H). LC-MS: M$^+$ calcd MW 738.85 uma, measured 739.20 m/z.

Synthesis of [Ir(ppy)$_2$(pic-3-OC$_6$H$_{12}$OSO$_3^-$)]TBA$^+$ [402]

Scheme 18: Synthesis of [402]

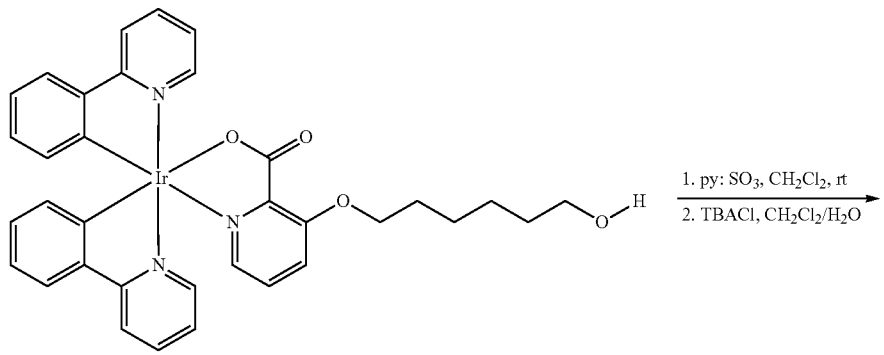

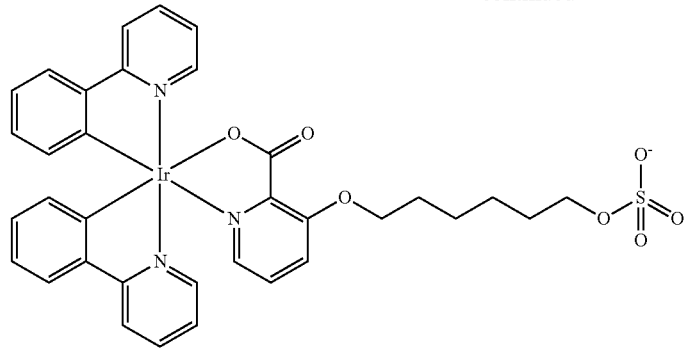

The hemi-sulfate Iridium derivative is prepared via sulfonation of the corresponding 3-alkoxypicolinate Iridium specie as depicted in Scheme 18.

In a typical synthesis [Ir(ppy)$_2$(pic-3-OC$_6$H$_{12}$OH)] [601] (475.0 mg, 0.64 mmol), 10 equivalents of sulphur trioxide-pyridine complex (py:SO$_3$, 1049.0 mg, 6.59 mmol) and 420 μL of anhydrous pyridine are dissolved in 10.5 mL of dry CH$_2$Cl$_2$. The resulting suspension is stirred overnight at room temperature. The suspension is filtered over a glass frit (IV) in order to remove the excess of py:SO$_3$, then the solid is washed with 15 mL of CH$_2$Cl$_2$. Finally, 15 mL of AcOEt are added and the resulting mixture is dried, yielding a yellow solid. About 2 g of tetrabutylammonium chloride are added at the entire crude product and they are dissolved in 30 mL of CH$_2$Cl$_2$, then 100 mL of distilled water yielded a biphasic mixture, which is stirred for 30 min. The organic layer is washed 8×200 mL of distilled H$_2$O, dried over Na$_2$SO$_3$, the volume reduced till half part and 20 mL of AcOEt are added. During the concentration, the product [402] appeared like a yellow solid, which is washed 2×20 mL of Et$_2$O, dried and weighted (560 mg, yield 82%).

$^1$H-NMR (300 MHz, DMSO-d$_6$, δ): 0.93 ppm (12H, t, —CH$_3$), 1.2-1.65 ppm (22H), 1.75 ppm (2H), 3.15 ppm (8H), 3.65 ppm (2H, t), 4.10 ppm (2H), 6.02 ppm (1H, dd), 6.21 ppm (1H, dd), 6.64-6.78 ppm (2H), 6.80-6.90 ppm (2H, dt), 7.22 ppm (2H, td), 7.41 ppm (2H, m), 7.58 ppm (1H), 7.78 ppm (3H), 7.92 ppm (2H, m), 8.18 ppm (2H), 8.55 ppm (1H). LC-MS: M$^+$ calcd MW 817.91 uma, measured 818.15 m/z.

Synthesis of [Ir(ppy)$_2$(pic-3-OC$_6$H$_{12}$OSO$_3$$^-$)] [Ir(piq)$_2$(bpy)]$^+$ [700]

Scheme 19: Synthesis of [700]

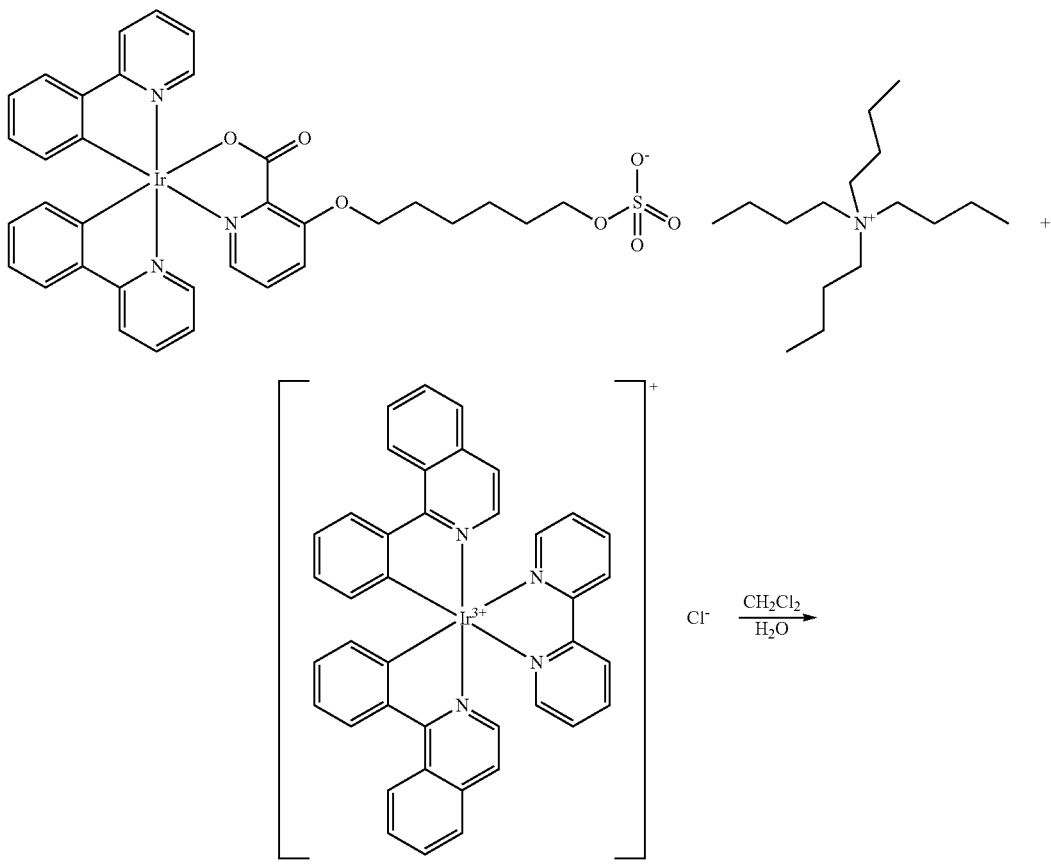

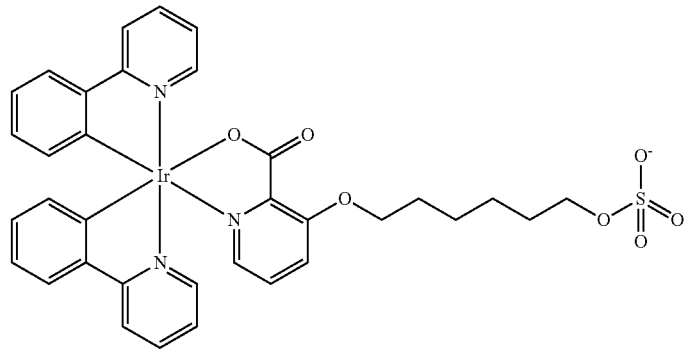
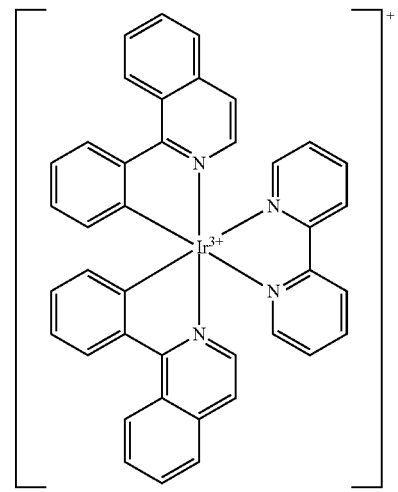

The titled complex is prepared from a strictly equimolar $CH_2Cl_2$ solution of the two starting complexes in the following way (see also Scheme 19).

The complexes $[Ir(ppy)_2(pic-3-OC_6H_{12}OSO_3^-)]TBA^+$ [402] (420.1 mg, 0.395 mmol) and $[Ir(piq)_2(bpy)]Cl$ [303] (314.8 mg, 0.395 mmol) are dissolved together in 210 mL of $CH_2Cl_2$. In order to remove the TBACl, the resulting solution is washed 8 times with 300 mL of distilled $H_2O$. The organic layer is dried over $Na_2SO_4$ and the volume is reduced. At the remaining solution, 60 mL of a 3:1 v/v mixture of $Et_2O$ and n-hexane are added. The slightly opaque resulting mixture is concentrated and 20 mL of the same $Et_2O$/n-hexane mixture aided to precipitate an orange-red solid. The product [700] is washed with 50 mL of $Et_2O$, dried and weighted (499 mg, yield 79.9%).

$^1$H-NMR (300 MHz, $CH_2Cl_2$, δ): 1.40 ppm (6H), 1.80 ppm (2H), 3.84 ppm (2H), 4.01 ppm (2H), 6.09 ppm (1H), 6.25 ppm (3H), 6.68 ppm (2H), 6.74-6.87 ppm (4H), 6.91 ppm (1H), 7.02-7.15 ppm (4H), 7.22-7.4 ppm (8H), 7.46-7.86 ppm (15H), 8.03 ppm (2H), 8.24 ppm (2H), 8.64 ppm (1H), 8.82 ppm (2H), 8.89 ppm (2H). Elemental analysis: found: C, 54.23/54.17%, H, 4.10/4.01%, N, 5.92/5.92%, Ir 25.2%; calcd. C, 56.44%, H, 3.78%, N, 6.23%, Ir 24.41%. Melting point: 258° C.

Synthesis of the Complex $[Ru(bp)_2(ppy)]^+CF_3SO_3^-$ [305]

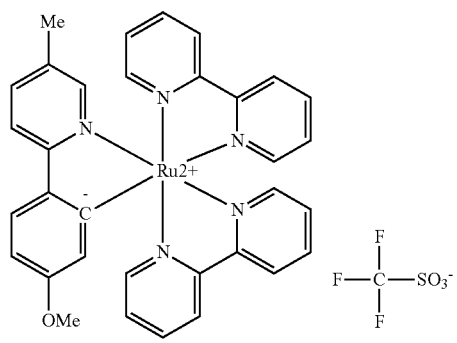

wherein Me stands for methyl, is carried out in accordance to Sasaki et al., Eur. J. Inorg. Chem. 2006, 3294.

Synthesis of the Salt [505]

Scheme 20: Synthesis of [505]

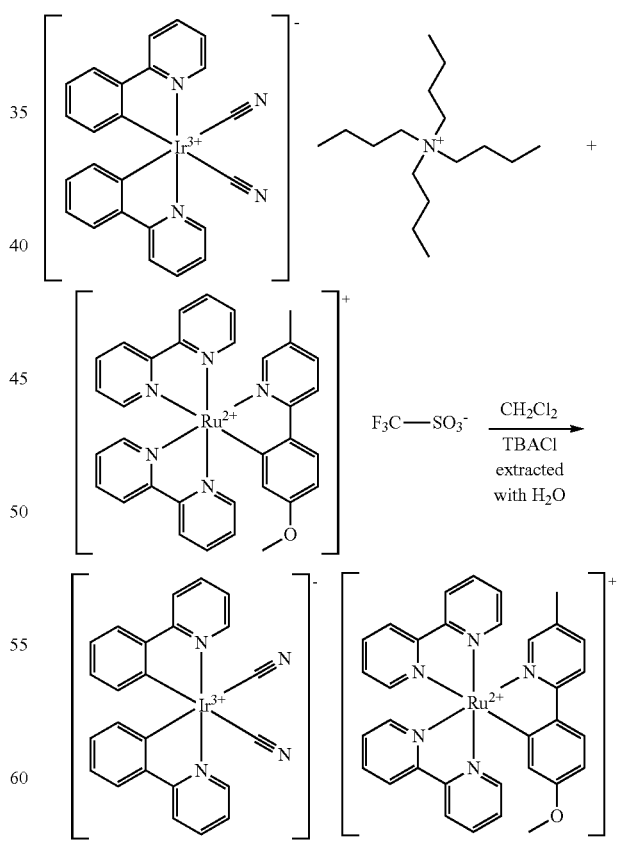

The double complex salt [505] is prepared from a strictly equimolar $CH_2Cl_2$ solution of the two starting complexes in the following way (see also Scheme 20).

The complexes [Ir(ppy)$_2$(CN)$_2$]TBA [400] and [Ru(bp)$_2$(ppy)]$^+$CF$_3$SO$_3^-$ [305] (each 0.926 mmol) are dissolved together in 300 mL of CH$_2$Cl$_2$. In order to remove the TBACl, the resulting solution is washed 8 times with 600 mL of distilled H$_2$O. The volume of the organic layer is reduced and then 120 mL of a 3:1 v/v mixture of Et$_2$O and n-hexane are added. The opaque resulting mixture is concentrated and 80 mL of the same Et$_2$O/n-hexane mixture aided to precipitate a yellow solid. The product [505] is re-precipitated again from CH$_2$Cl$_2$ and 3:1 v/v Et$_2$O and n-hexane, dried and weighted.

Photo Physical Data
UV/VIS:
General Information

The UV-visible absorption spectra are recorded by using a Cary 5000 UV-visible/near-infrared spectrophotometer and are baseline- and solvent-corrected. All the solvents used are spectroscopic grade and all the samples had a concentration of 1×10$^{-5}$ M. All spectra are recorded in quartz cuvettes (1 cm, Hellma), which for the oxygen free measurements have been modified for the freeze-pump-thaw technique such that the cuvette can be connected to high vacuum. Results are shown in the following table. The degassing procedures are repeated until the vacuum in the cuvette reached approximatively 10$^{-6}$ mbar.

TABLE

UV/VIS Data (solutions in DCM, degassed)

| Compound | $\lambda_{max}$ (nm) |
|---|---|
| [500] | 256, 305 (shoulder) |
| [501] | 254, 305 (shoulder) |
| [502] | 254, 305 (shoulder) |
| [503] | 229, 270, 290, 387 (shoulder) |

Phosphorescence Life Time:
General Information

Time-resolved luminescence experiments are performed by using a HORIBA Jobin-Yvon IBH FL-322 Fluorolog 3 spectrometer equipped with NanoLED (402 nm, FWHM<750 ps) with repetition rates between 10 kHz and 1 MHz, used to excite the sample, double-grating excitation and emission monochromators, and a TBX-4-X single-photon-counting as detector. The measurements are performed by using the time-correlated single-photon-counting (TC-SPC) option on the Fluorolog 3 instrument. The goodness-of-fit is assessed by minimising the reduced $\chi^2$ function and by visual inspection of the weighted residuals.

All the solvents used are spectroscopic grade. All the samples had a concentration of 1×10$^{-5}$ M. All spectra are recorded in quartz cuvettes (1 cm, Hellma), which for the oxygen free measurements have been modified for the freeze-pump-thaw technique such that the cuvette can be connected to high vacuum. Results are shown in the following table. The degassing procedures are repeated until the vacuum in the cuvette reached approximatively 10$^{-6}$ mbar.

TABLE

Phosphorescence lifetime (solutions in DCM, degassed)

| Compound | $\lambda_{em}$ | | |
|---|---|---|---|
| | 473 nm | 600 nm | 680 nm |
| [500] | 1.05 µs (87%)<br>3.73 µs (13%) | 561 ns | 555 ns |
| [501] | 1.28 µs (88%)<br>3.66 µs (21%) | 596 ns (81%)<br>1.42 µs (19%) | 583 ns (73%)<br>1.28 µs (22%) |
| [502] | 1.23 µs (65%)<br>4.02 µs (35%) | 1.19 µs | 1.06 µs (76%)<br>1.63 µs (24%) |
| [503] | 1.12 µs (85%)<br>4.49 µs (15%) | 1.09 µs | 1.08 µs |

Photoluminescence Efficiency:
General Information

Steady-state experiments are performed by using a HORIBA Jobin-Yvon IBH FL-322 Fluorolog 3 spectrometer equipped with a 450 W xenon arc lamp, double-grating excitation and emission monochromators, and a TBX-4-X single-photon-counting as detector. Emission spectra are corrected for source intensity (lamp and grating) and emission spectral response (detector and grating) by standard correction curves.

All the solvents used are spectroscopic grade and all the samples had a concentration of 1×10$^{-6}$ M. All spectra are recorded in quartz cuvettes (1 cm, Hellma), which for the oxygen free measurements have been modified for the freeze-pump-thaw technique such that the cuvette can be connected to high vacuum. The degassing procedures are repeated until the vacuum in the cuvette reached approximatively 10$^{-6}$ mbar.

Luminescence quantum yields (Φ) are measured in optically dilute solutions (degassed, OD<0.1 at excitation wavelength) using DCM as a solvent and using the integrating sphere method. The data are collected with a Hamamatsu PMA-12 Spectral Measurement System, equipped with a 150 W Xenon arc lamp, grating monochromator, CCD area image sensor as multi-channel photo-detector, optical fiber and control circuit. All the measurements are corrected taking into consideration the sample holder geometry and solvent presence. Results are shown in the following table.

TABLE

Luminescence quantum yields Φ

| Compound | Φ | $\lambda_{max\ emission}$ |
|---|---|---|
| [500] | 0.19 | 472, 502, 589 |
| [501] | 0.34 | 453, 481, 589 |
| [502] | 0.54 | 512 |
| [503] | 0.52 | 589 |

Excitation wavelenght: 366 nm

Electroluminescent Devices
General Information
Device Characterization

Prior to the deposition of the active layer, a thin layer (100 nm) of polyethylenedioxythiophene:polystyrene sulfonic acid (PEDOT:PSS) is spin-coated. The active layer is spin-coated from acetonitrile solution and has a thickness of 70 nm. The active layer is composed of the compounds. In some devices small amounts of the ionic liquid (IL) 1-butyl-3-methylimidazolium hexafluorophosphate is added to speed up the turn-on of the device. The molar ratio between iTMC and IL molecules is 2:1. An 80 nm thick aluminum layer is evaporated and used as the cathode. Structured ITO-containing glass plates are used as the substrates. Device preparation and characterization are performed in inert atmosphere inside a glove box. (<0.1 ppm H$_2$O and <0.1 ppm O2). Quantum efficiency (EQE), max. luminance (cd/m2) and the operating time required for reaching it, the efficacy (cd/A) and the devices' half life time (if detected) are compiled in the following tables.

TABLE

Luminescent devices operated with 5 Volt

| Compound | EQE | Max. Luminance (cd/m$^2$) | Efficacy (cd/A) | Turn on time to get max. brightness (min.) | $T_{1/2}$ (hours) |
|---|---|---|---|---|---|
| [500] | 0.046 | 30.4 | 0.13 | 126 | 7 |
| [501] | 0.030 | 1.6 | 0.0018 | 331 | n.d. |
| [502] | 0.012 | 1 | 0.089 | 342 | n.d. |
| [503] | 0.085 | 19 | 0.130 | 702 | 26 |

TABLE

Luminescent devices operated with 7 Volt

| Compound | EQE | Max. Luminance (cd/m$^2$) | Efficacy (cd/A) | Turn on time to get max. brightness (min.) | $T_{1/2}$ (hours) |
|---|---|---|---|---|---|
| [500] | 0.089 | 99.3 | 0.250 | 32 | 1.4 |
| [501] | 0.306 | 22.0 | 0.910 | 18 | 0.44 |
| [502] | 0.015 | 10.0 | 0.036 | 0.18 | 0.11 |
| [503] | 0.072 | 244.0 | 0.110 | 8.4 | 0.16 |

The invention claimed is:

1. A salt of an organometallic complex cation and an organometallic complex anion, wherein the cation as well as the anion consists of a central metal atom M of atomic weight greater than 40 associated to 2 or more ligands,
   at least one ligand comprising a cyclic organic moiety with a carbon atom bonding to M, and
   at least one ligand comprising a cyclic organic moiety with a nitrogen atom bonding to M,
   wherein each the anion and the cation, independently, conforms to the formula I

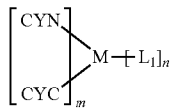

(I)

wherein M is a metal of atomic weight greater than 40,
CYC is a cyclic organic moiety with a carbon atom bonding to M,
CYN is a cyclic organic moiety with a nitrogen atom or carbene bonding to M,
$L_1$ bonding to M is selected from inorganic and organic ligands, wherein
$L_1$ as a neutral ligand is selected from bipyridine and phenanthroline, each of which is unsubstituted or substituted by halogen, $C_1$-$C_4$haloalkyl, $C_1$-$C_4$alkyl, $C_1$-$C_4$alkoxy, phenyl, halophenyl;
$L_1$ as a cationic ligand is selected from the above neutral ligands which carry, in addition, a cationic substituent; and
$L_1$ as an anionic ligand is selected from halogenide and cyano; pyridylcarboxylate which is unsubstituted or substituted by halogen, $C_1$-$C_4$haloalkyl, $C_1$-$C_4$alkyl, $C_1$-$C_4$alkoxy or an anionic substituent; and from the above neutral ligands which carry, in addition, an anionic substituent,
where any ionic substituent is selected from groups of the formula —X'-(spacer)$_x$-Y'; where X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from COO$^-$, SO$_3^-$, OSO$_3^-$, or a cationic group selected from NR$_3^+$, and R is H or $C_1$-$C_{12}$alkyl,
m is a number from 1 to 3,
n is a number from 0 to 4,
with the proviso that (m+n) is from the range 2 to 5, and
wherein the salt is essentially free of non-complex ions, whose concentration is below 5% by weight of the salt.

2. The salt of claim 1, wherein the net charge of the central metal atom M and its ligands in the cation is +1 and in the anion is −1.

3. The salt of claim 1 conforming to the formula II

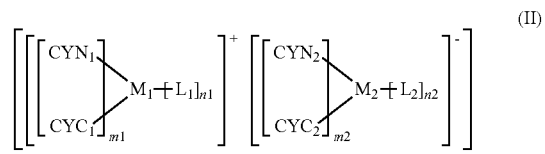

(II)

wherein
$M_1$ and $M_2$ are selected from metals as defined for M,
CYC$_1$ and CYC$_2$ are cyclic organic moieties as defined for CYC,
CYN$_1$ and CYN$_2$ are cyclic organic moieties as defined for CYN,
$L_2$ is independently as defined for $L_1$,
$m_1$ and $m_2$ are numbers as defined for m,
$n_1$ and $n_2$ are numbers as defined for n,
with the proviso that
i) each of (m$_1$+n$_1$) and (m$_2$+n$_2$) is from the range 2 to 5,
ii) the sum of charges in [CYC$_1$ CYN$_1$] multiplied by m1+L$_1$ multiplied by n1+M$_1$ is +1, and
iii) the sum of charges in [CYC$_2$ CYN$_2$] multiplied by m2+L$_2$ multiplied by n2+M$_2$ is −1.

4. The salt of claim 1 wherein, independently,
CYC and CYN are interlinked by one or more chemical bonds to form a bidentate ligand selected from

(VI-1)

(VI-2)

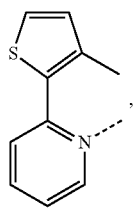 (VI-3)
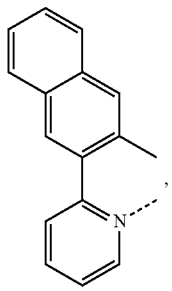 (VI-4)
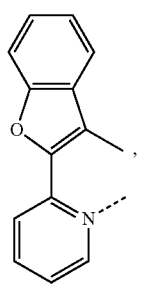 (VI-5)
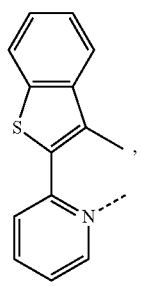 (VI-6)
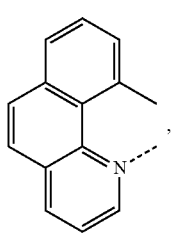 (VI-7)
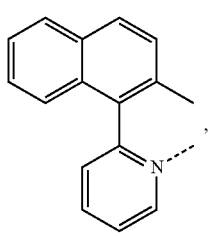 (VI-8)
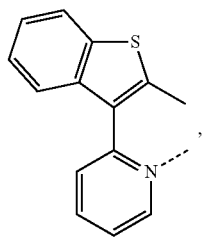 (VI-9)
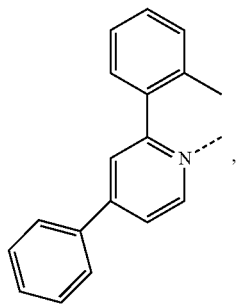 (VI-10)
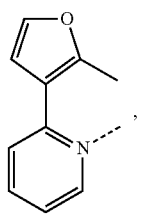 (VI-11)
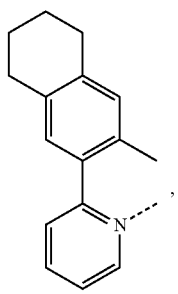 (IV-12)
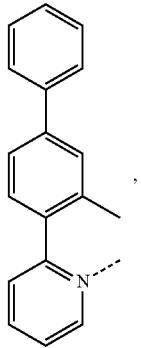 (VI-13)

(VI-14) 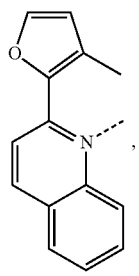
(VI-15) 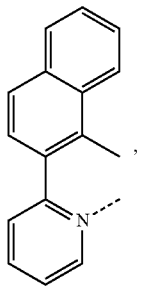
(VI-16) 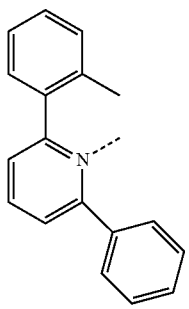
(VI-17) 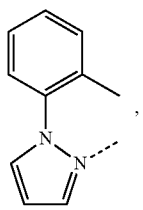
(VI-18) 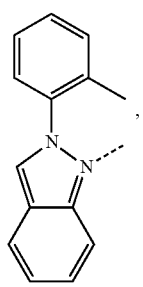
(VI-19) 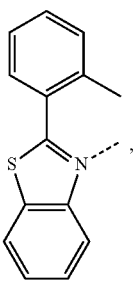
(VI-20) 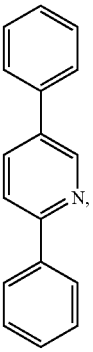
(VI-21) 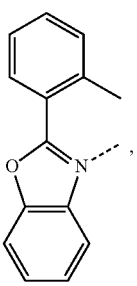
(VI-22) 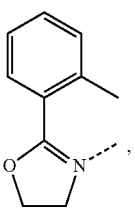
(VI-23) 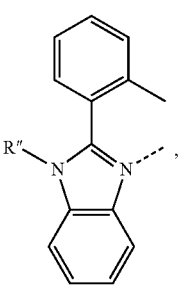

(VI-24) 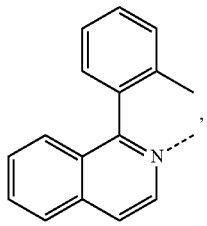

(VI-25) 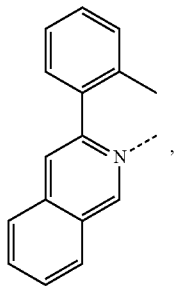

(VI-26) 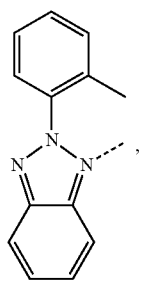

(VI-27) 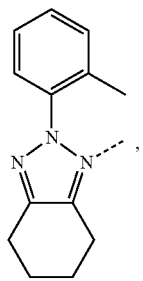

(VI-28) 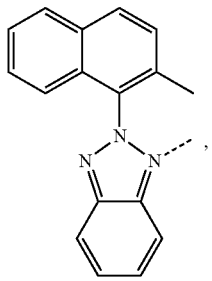

(VI-29) 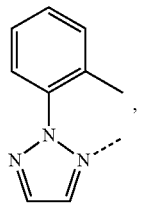

(VI-30) 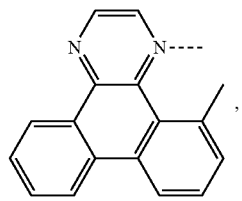

wherein the dashed line in each formula indicates the N-metal bond while the straight line in each formula indicates the carbon-metal bond, and wherein carbon atoms not bonding to metal are unsubstituted or substituted;

M is selected from Tl, Pb, Bi, In, Sn, Sb, Te, Mo, Cr, Mn, Ta, V, Zn, Fe, Ni, Co, Rh, Re, Os, Ag, Au, lanthanides including Eu, Tb, Nd, Yb, Er, and Cu, Ru, Ir, Pt, Pd; and any substituent, if present, is selected from halogen, hydroxy, $C_1$-$C_8$alkyl, $C_1$-$C_8$-fluoroalkyl, $C_1$-$C_8$alkoxy, phenyl, phenyloxy, COR, OCOR, COOR, $SO_2R$, CN, NHR NRR', and ionic substituents —X'-(spacer)$_x$-Y'; where R, R' independently are selected from $C_1$-$C_{12}$alkyl or together are pentylene or $(CH_2)_2O(CH_2)_2$ or $(CH_2)_2NH(CH_2)_2$ and R may also be hydrogen; X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from $COO^-$, $OCOO^-$, $SO_3^-$, $OSO_3^-$, $PO_3^{2-}$, $OPO_3^{2-}$, or a cationic group selected from $NR_3^+$.

5. The salt of claim 1 wherein, independently, the metal M is selected from Ir and Pt, CYC and CYN are interconnected to commonly form a bidentate ligand selected from 2-phenylpyridines of the formulae (VI-1) 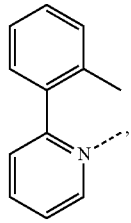

(VI-4) 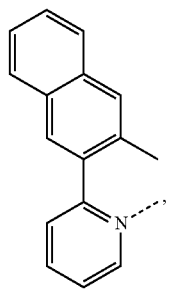

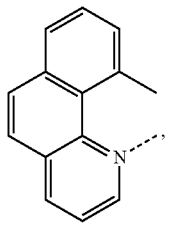

(VI-7)

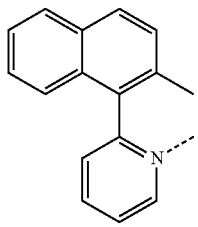

(VI-8)

which are unsubstituted or substituted by halogen, $C_1$-$C_4$haloalkyl, $C_1$-$C_4$alkyl or $C_1$-$C_4$alkoxy or by a ionic substituent;

where any ionic substituent is selected from groups of the formula —X'-(spacer)$_x$-Y'; where X' is a direct bond, O, S, CO, COO, COCO, NR, phenylene; x is 0 or 1; spacer is $C_1$-$C_{12}$alkylene, $C_2$-$C_{12}$alkylene which is interrupted by X', phenylene, $C_2$-$C_{12}$alkenylene; Y' is an anionic group selected from COO$^-$, SO$_3^-$, OSO$_3^-$, or a cationic group selected from NR$_3^+$, and R is H or $C_1$-$C_{12}$alkyl.

6. An organic electronic device, comprising an emitting or conducting layer which contains a salt according to claim 1.

7. The device of claim 6, further comprising a hole transport material, selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N-bis(4-ethylphenyl)-[1,1'-(3,3'-dimethyl)biphenyl]4,4'-diamine (ETPD), tetrakis-(3-methylphenyl)-N,N,N',N-2,5-phenylenediamine (PDA), a-phenyl-4-N,N-diphenylaminostyrene (TPS), p-(diethylamino)benzaldehyde-diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, (phenylmethyl) polysilane, poly(3,4-ethylendioxythiophene) (PEDOT), polyaniline, and combinations thereof, or one or more of the above components doped into a polymer.

8. A device selected from stationary and mobile displays, including displays for computers, mobile phones, laptops, pdas, TV sets, displays in printers, kitchen equipment, billboards, lightings, information boards and destination boards for example in trains and buses, containing an organic light emitting diode or light emitting cell according to claims 6.

9. A method of using a salt according to claim 1, the method comprising: adding the salt according to claim 1 in an electronic device, as conductor or ionic liquid in a photovoltaic device or in a battery, as an oxygen sensitive indicator, as a pH sensitive indicator, as a phosphorescent indicator in a bioassay, or as a catalyst.

10. A method for the preparation of a light emitting device, which method comprises providing an organic substance layer containing a complex salt according to claim 1 between a pair of electrodes on a substrate.

11. The method according to claim 10 for the preparation of an organic light emitting diode or light emitting cell wherein a fraction or all light emission is white light, wherein the complex salt contains ions whose light emission essentially is of complementary colour.

12. Process for the preparation of a salt of an organometallic complex cation and an organometallic complex anion as defined in claim 1, which process comprises
   i) combining equivalent amounts of a compound comprising a cyclometallated complex anion of a metal M and a non-complex organic or inorganic cation with a compound comprising a cyclometallated complex cation of a metal M and a i.e. non-complex inorganic anion, preferably in the form of a solution and/or dispersion,
   ii) subjecting the combination obtained in step (i) to a technique substantially reducing the concentration of non-complex anions and cations, such as extraction or dialysis using a polar solvent,
   iii) and, optionally, isolating the complex salt of claim 1.

* * * * *